United States Patent
Cha et al.

(10) Patent No.: US 7,947,806 B2
(45) Date of Patent: May 24, 2011

(54) MUSSEL BIOADHESIVE

(75) Inventors: Hyung Joon Cha, Pohang (KR); Dong Soo Hwang, Gwangju (KR); Young Soo Gim, Gwangju (KR); Oh-Gi Jung, legal representative, Gwangju (KR)

(73) Assignees: POSTECH Foundation, Hyoja-dong, Nam-ku, Pohang, Kyungsangbuk-do (KR); POSCO, Goedong-dong, Nam-ku, Pohang-shi, Kyungsangbuk-do (KR)

( * ) Notice: Subject to any disclaimer, the term of this patent is extended or adjusted under 35 U.S.C. 154(b) by 138 days.

(21) Appl. No.: 11/911,004

(22) PCT Filed: Apr. 7, 2006

(86) PCT No.: PCT/KR2006/001283
§ 371 (c)(1),
(2), (4) Date: Jun. 20, 2008

(87) PCT Pub. No.: WO2006/107183
PCT Pub. Date: Oct. 12, 2006

(65) Prior Publication Data
US 2009/0203883 A1    Aug. 13, 2009

Related U.S. Application Data

(60) Provisional application No. 60/669,667, filed on Apr. 8, 2005.

(51) Int. Cl.
*C07K 14/00* (2006.01)
*C12P 21/06* (2006.01)
(52) U.S. Cl. ...................... 530/350; 435/69.1
(58) Field of Classification Search .......... None
See application file for complete search history.

(56) References Cited

U.S. PATENT DOCUMENTS 5,202,236 A * 4/1993 Maugh et al. ............... 435/69.1
6,451,579 B1 * 9/2002 Jessee et al. ............... 435/235.1

FOREIGN PATENT DOCUMENTS

JP    08-266282 A    * 10/1996

OTHER PUBLICATIONS

Inoue et al., Cloning, sequencing and sites of expression of genes for the hydroxyarginine-containing adhesive-plaque protein of the mussel *Mytilus galloprovincialis*, Eur. J. Biochem. 239:172-176, 1996.*
English Machine translation from Japanese of JP08-266282-A, Nov. 18, 2009.*
NCBI Accession No. BAB16314 (Oct. 4, 2000).
Hwang, D.S., et al. "Expression of Functional Recombinant Mussel Adhesive Protein Mgfp-5 in *Escherichia coli*" Applied and Environmental Microbiology, vol. 70 (6): pp. 3352-3359 (Jun. 2004).
NCBI Accession No. Q27409(Jan. 25, 2005).
Miki, D., et al. "Expression Sites of Two Byssal Protein Genes of *Mytilus galloprovincialis*" Biol. Bull., vol. 190: pp. 213-217 (Apr. 1996).

* cited by examiner

*Primary Examiner* — Elly-Gerald Stoica
(74) *Attorney, Agent, or Firm* — Lexyoume IP Group, PLLC.

(57) ABSTRACT

The present invention relates to a bioadhesive derived from mussel. In particular, it relates to a novel MGFP-3A MUTANT(*Mytilus galloprovincialis* foot protein type-3A MUTANT) protein and a recombinant protein that is a hybrid of MGFP-3A MUTANT, FP(Foot Protein)-1 and MGFP-5 (*Mytilus galloprovincialis* foot protein type-5). According to the present invention, the adhesive protein can be economically produced in large scale and can be used instead of chemical adhesives.

7 Claims, 26 Drawing Sheets

1. marker
2. cell disrupt
3. eluant
4. buffer C
5. buffer D
6. buffer E
7. dialysis & freeze-drying 1. marker
2. cell disrupt
3. eluant
4. buffer C
5. buffer D
6. buffer E
7. dialysis & freeze-drying 1 : Cell disrupt   2 : Eluant
3 : Buffer C   4 : Buffer D   5 : Buffer E 1 : Cell disrupt   2 : Eluant
3 : Buffer C   4 : Buffer D   5 : Buffer E 1 : Cell disrupt   2 : Eluant
3 : Buffer C   4 : Buffer D   5 : Buffer E

FIG. 20A

[SEQ ID NO: 1] Primer MGFP-3A Mutant-U
5'-GGG GCT AGC GCT GAT TAT TAT GGT CCA AAG-3'
         NheI

[SEQ ID NO: 2] Primer MGFP-3A Mutant-D
5'-CCC GGA TCC TTA ATA ATA CTT TCG TCC-3'
       BamHI

[SEQ ID NO: 3] Primer ENG353F1
5'-GGG CAT ATG GCT GAT TAT TAT GGT CCA-3'
       NdeI

[SEQ ID NO: 4] Primer ENG353R1
5'- CCC GAA TTC ATA ATA CTT TCG TCC CCA-3'
       EcoRI

[SEQ ID NO: 5] Primer ENG353F2
5'-GGG GAA TTC AGT TCT GAA GAA TAC AAA-3'
       EcoRI

[SEQ ID NO: 6] Primer ENG353R2
5'-CCC AAG CTT ACT GCT ACC ACC TCC ATA-3'
       HindIII

FIG. 20B

[SEQ ID NO: 7] Primer ENG353F3
5'-GGG <u>AAG CTT</u> GCT GAT TAT TAT GGT CCA-3'
         *Hind* III

[SEQ ID NO: 8] Primer ENG353R3
5'-GGG <u>CTC GAG</u> ATA ATA CTT TCG TCC CCA TCG-3'
         *Xho* I

[SEQ ID NO: 9] Primer ENG153F
5'-CAT CAT GGT ATG <u>CAT ATG</u> GCT AAA CCG-3'
                    *Nde* I

[SEQ ID NO: 10] Primer ENG153R
5'- TTC TTC AGA ACT <u>GGA TTC</u> TTT GTA AGT-3'
                    *EcoR* I

[SEQ ID NO: 11] Primer ENG351F
5'- CAT CAT GGT ATG <u>AAG CTT</u> GCT AAA CCG-3'
                    *Hind* III

[SEQ ID NO: 12] Primer ENG351R
5'-TTC TTC AGA ACT <u>CTC GAG</u> TTT GTA AGT-3'
                    *Xho* I

FIG. 20C

[SEQ ID NO: 13] MGFP-3A coding sequence
GCTGATTATTATGGTCCAAAGTATGGTCCTCCAAGACGCTACGGTGGTGGCAACTACAATAGA
TATGGCAGACGTTATGGCGGGTATAAAGGCTGGAACAATGGTTGGAAAAGAGGTCGATGGGGA
CGAAAGTATTATTGA

[SEQ ID NO: 14] MGFP-3A amino acid sequence
ADYYGPKYGPPRRYGGGNYNRYGRRYGGYKGWNNGWKRGRWGRKYY

[SEQ ID NO: 15] MGFP-5 coding sequence
AGTTCTGAAGAATACAAAGGTGGTTATTACCCAGGCAATACTTACCACTATCATTCAGGTGGT
AGTTATCACGGATCCGGCTATCATGGAGGATATAAGGGAAAGTATTACGGAAAGGCAAAGAAA
TACTATTATAAATATAAAAACAGCGGAAAATACAAGTATCTGAAGAAAGCTAGAAAATACCAT
AGAAAGGGTTACAAGAAGTATTATGGAGGTGGTAGCAGTTAG

[SEQ ID NO: 16] MGFP-5 amino acid sequence
SSEEYKGGYYPGNTYHYHSGGSYHGSGYHGGYKGKYYGKAKKYYYKYKNSGKYKYLKKARKYHRK
GYKKYYGGGSS

[SEQ ID NO: 17] 6xAKPSYPPTYK cDNA
(6 times repeated sequence derived from mytilus edulis foot protein-1)
GCTAAACCGTCTTACCCGCCGACCTACAAAGCAAAACCCTCGTACCCACCGACTTATAAGGCTA
AACCTAGCTATCCACCTACGTACAAAGCTAAACCGTCTTACCCGCCGACTTACAAAGCAAAACC
GTCCTACCCTCCGACCTATAAGGCTAAACCGAGTTACCCCCGACTTACAAA

[SEQ ID NO: 18] 6xAKPSYPPTYK amino acid sequence
AKPSYPPTYKAKPSYPPTYKAKPSYPPTYKAKPSYPPTYKAKPSYPPTYKAKPSYPPTYK

FIG. 20D

[SEQ ID NO: 19] MGFP-353 coding sequence
ATGGCTGATTATTATGGTCCAAAGTATGGTCCTCCAAGACGTTACGGTGGTGGCAACTACAAT
AGATATGGCAGACGTTATGGCGGGTATAAAGGCTGGAACAATGGTTGGAAAAGAGGTCGATGG
GGACGAAAGTATTATGAATTCAGTTCTGAAGAATACAAAGGTGGTTATTACCCAGGCAATTCG
AACCACTATCATTCAGGTGGTAGTTATCACGGATCCGGCTACCATGGAGGATATAAGGGAAAG
TATTACGGAAAGGCAAAGAAATACTATTATAAATATAAAAACAGCGGAAAATACAAGTATCTA
AAGAAAGCTAGAAAATACCATAGAAAGGGTTACAAGAAGTATTATGGAGGTGGTAGCAGTAAG
CTTGCTGATTATTATGGTCCAAAGTATGGTCCTCCAAGACGTTACGGTGGTGGCAACTACAAT
AGATATGGCAGACGTTATGGCGGGTATAAAGGCTGGAACAATGGTTGGAAAAGAGGTCGATGG
GGACGAAAGTATTATCTCGAG

[SEQ ID NO: 20] MGFP-353 amino acid sequence
MADYYGPKYGPPRRYGGGNYNRYGRRYGGYKGWNNGWKRGRWGRKYYEFSSEEYKGGYYPGNSN
HYHSGGSYHGSGYHGGYKGKYYGKAKKYYYKYKNSGKYKYLKKARKYHRKGYKKYYGGGSSKLAD
YYGPKYGPPRRYGGGNYNRYGRRYGGYKGWNNGWKRGRWGRKYYLE

FIG. 20E

[SEQ ID NO: 21] MGFP-153 coding seqeucne
ATGGCTAAACCGTCTTACCCGCCGACCTACAAAGCAAAACCCTCGTACCCACCGACTTATAAGG
CTAAACCTAGCTATCCACCTACGTACAAAGCTAAACCGTCTTACCCGCCGACTTACAAAGCAAA
ACCGTCCTACCCTCCGACCTATAAGGCTAAACCGAGTTACCCCCGACTTACAAAGAATTCAGT
TCTGAAGAATACAAAGGTGGTTATTACCCAGGCAATTCGAACCACTATCATTCAGGTGGTAGT
TATCACGGATCCGGCTACCATGGAGGATATAAGGGAAAGTATTACGGAAAGGCAAAGAAATAC
TATTATAAATATAAAAACAGCGGAAAATACAAGTATCTAAAGAAAGCTAGAAAATACCATAGA
AAGGGTTACAAGAAGTATTATGGAGGTGGTAGCAGTAAGCTTGCTGATTATTATGGTCCAAAG
TATGGTCCTCCAAGACGTTACGGTGGTGGCAACTACAATAGATATGGCAGACGTTATGGCGGG
TATAAAGGCTGGAACAATGGTTGGAAAAGAGGTCGATGGGGACGAAAGTATTATCTCGAG

[SEQ ID NO: 22] MGFP-153 amino acid sequence
MAKPSYPPTYKAKPSYPPTYKAKPSYPPTYKAKPSYPPTYKAKPSYPPTYKAKPSYPPTYKEFSSEE
YKGGYYPGNSNHYHSGGSYHGSGYHGGYKGKYYGKAKKYYYKYKNSGKYKYLKKARKYHRKGYKK
YYGGGSSKLADYYGPKYGPPRRYGGGNYNRYGRRYGGYKGWNNGWKRGRWGRKYYLEHHHHHH

FIG. 20F

[SEQ ID NO: 23] MGFP-351 coding sequence
ATGGCTGATTATTATGGTCCAAAGTATGGTCCTCCAAGACGTTACGGTGGTGGCAACTACAAT
AGATATGGCAGACGTTATGGCGGGTATAAAGGCTGGAACAATGGTTGGAAAAGAGGTCGATGG
GGACGAAAGTATTATGAATTCAGTTCTGAAGAATACAAAGGTGGTTATTACCCAGGCAATTCG
AACCACTATCATTCAGGTGGTAGTTATCACGGATCCGGCTACCATGGAGGATATAAGGGAAAG
TATTACGGAAAGGCAAAGAAATACTATTATAAATATAAAAACAGCGGAAAATACAAGTATCTA
AAGAAAGCTAGAAAATACCATAGAAAGGGTTACAAGAAGTATTATGGAGGTGGTAGCAGTAAG
CTTGCTAAACCGTCTTACCCGCCGACCTACAAAGCAAAACCCTCGTACCCACCGACTTATAAGG
CTAAACCTAGCTATCCACCTACGTACAAAGCTAAACCGTCTTACCCGCCGACTTACAAAGCAAA
ACCGTCCTACCCTCCGACCTATAAGGCTAAACCGAGTTACCCCCCGACTTACAAACTCGAG

[SEQ ID NO: 24] MGFP-351 amino acid sequence
MADYYGPKYGPPRRYGGGNYNRYGRRYGGVKGWNNGWKRGRWGRKYYEFSSEEYKGGYYPGNSN
HYHSGGSYHGSGYHGGYKGKYYGKAKKYYYKYKNSGKYKYLKKARKYHRKGYKKYYGGGSSKLAK
PSYPPTYKAKPSYPPTYKAKPSYPPTYKAKPSYPPTYKAKPSYPPTYKAKPSYPPTYKLE

MUSSEL BIOADHESIVE

CROSS-REFERENCE TO RELATED APPLICATION

This application is a National Stage application of PCT/KR2006/001283, filed Apr. 07, 2006, which claims priority to provisional Application No. 60/669,667, filed on Apr. 08, 2005.

BACKGROUND OF THE INVENTION (a) Field of the Invention

The present invention relates to a bio-adhesive derived from mussel, more particularly to a novel *Mytilus gallopro-vincialis* foot protein-3A (MGFP-3A) and a recombinant protein that is a hybrid of MGFP-3A, FP (Foot Protein)-1 and MGFP-5 (*Mytilus galloprovincialis* foot protein-5).

(b) Background of the Invention

Mussels produce and secrete specialized water-resistant bioadhesives, and have been studied as a potential source of water-resistant bioadhesives. They adhere tightly to surfaces underwater using the byssus secreted from the foot of the mussel. At the end of each thread is an adhesive plaque containing a water-resistant glue that enables the plaque to anchor to wet solid surfaces [Waite, J. H., Biology Review. 58:209-231 (1983)]. This strong and water-insoluble adhesion has attracted interest for potential use in biotechnological applications.

In addition, mussel adhesive proteins can also be used as medical adhesives as they are non-toxic to the human body and do not impose immunogenicity [Dove et al., Journal of American Dental Association. 112:879 (1986)]. Moreover, their biodegradable properties make them environmentally friendly.

The byssus can be divided into distal and proximal parts. The proximal part is connected to the stem gland of the mussel foot, while the distal part is connected to the adhesive plaques. The adhesive plaque is composed of five distinct types of proteins: foot protein type 1 (FP-1) to type 5 (FP-5) [Deming, T. J., Current Opinion in Chemical Biology. 3:100-105 (1999)].

All of the mussel adhesive proteins contain high ratios of 3,4-dihydroxyphenyl-L-alanine (DOPA), which is derived from hydroxylation of tyrosine residues [Waite, J. H., Biology Review. 58:209-231 (1983)]. The adhesive proteins closest to the adhesion interface have the highest proportion of DOPA residues [Waite, J. H., Integr. Comp. Biol. 42:1172-1180 (2002)]. In contrast, mussel adhesive protein analogs lacking DOPA show greatly reduced adhesion abilities [Yu et al., Journal of American Chemical Society. 121:5825-5826 (1999)]. Indeed, a biochemical study showed that DOPA residues can enable mussel adhesive protein molecules to cross-link with each other via oxidative conversion to DOPA o-quinone. Thus, the DOPA content of a mussel adhesive protein appears to be specifically related to its adhesive properties.

Currently Cell-Tak, a naturally extracted mussel adhesive protein product, is commercially available. This adhesive is mainly composed of FP-1 and FP-2 type proteins, with a minor portion of FP-3. However, the natural extraction process is labor-intensive and inefficient, requiring around 10,000 mussels for 1 g of protein [Morgan, D., The Scientist. 4:1-6 (1990)].

Therefore, researchers have sought to produce recombinant mussel adhesive proteins, for example FP-1, in expression systems such as *Escherichia coli* and yeast.

However, these previous studies failed to express functional and economical mussel adhesive proteins due to a number of complications, including a highly biased amino acid composition (5 amino acid types comprise ~89% of the total amino acids in FP-1), different codon usage preferences between mussel and other expression systems (tRNA utilization problems) and low protein yields [U.S. Pat. No. 5,242,808, Filpula et al., Biotechnol. Prog. 6:171-177 (1990), Salerno et al., Applied Microbiology and Biotechnology 58:209-214 (1993), Kitamura et al., Journal of Polymer Science Part A: Polymer Chemistry, 37:729-736 (1999)].

The inventors of the present invention have separated MGFP-5 encoding a novel adhesion protein from a mussel and established a expression system for the production of an adhesion protein that is more adhesive than a FP-1 and is from a mussel (WO 05/02920) to overcome the problems in the prior art.

However, MGFP-5 has drawback of a low producing yield, and a necessity of improving solubility. And so, the inventors improve yield and solubility of polypeptide by developing the chimeric gene with FP-1 and MGFP-5 (WO 05/02920).

Therefore, an adhesive having excellent physicochemical properties including an adhesion force can be developed by combination with MGFP-5 and existing or novel polypeptide of a mussel.

SUMMARY OF THE INVENTION

To overcome the aforementioned problems in the prior art, an objective of the present invention is to provide a novel adhesive protein derived from a mussel.

Another object of the present invention is to provide a novel recombinant adhesive protein which comprises MGFP-3A MUTANT and at least two mussel adhesive proteins, and/or 6xAKPSYPPTYK and MGFP-5 fused at one or both ends of the MGFP-3A MUTANT.

Further object of the present invention is to provide a novel adhesive protein derived from *Mytilus galloprovincialis*.

The aforementioned adhesive protein preferably comprises the amino acid sequence shown in SEQ ID NO: 14 and the amino acid sequence shown in SEQ ID NO: 16.

The present invention also provides a recombinant adhesive protein where 6xAKPSYPPTYK or some amino acid sequences derived from MGFP-3A is attached to the carboxyl-terminus and/or amino-terminus of the MGFP-5, mussel adhesive protein.

An example of the aforementioned recombinant adhesive protein is an amino acid sequence selected from the group consisting of the amino acid sequence shown in SEQ ID NO: 20, the amino acid sequence shown in SEQ ID NO: 22, and the amino acid sequence shown in SEQ ID NO: 24.

Another objective of the present invention is to provide a novel gene coding a new adhesive protein derived from mussel.

The present invention provides a nucleotide sequence encoding the aforementioned novel adhesive protein derived from M galloprovincialis.

The examples of the aforementioned nucleotide sequence are the nucleotide sequence shown in SEQ ID NO: 13 and the nucleotide sequence shown in SEQ ID NO: 15.

The present invention also provides a recombinant adhesive protein where 6xAKPSYPPTYK or some amino acid sequences derived from MGFP-3A is attached to the carboxyl-terminus and/or amino-terminus of the MGFP-5, mussel adhesive protein.

The present invention provides a polynucleotide encoding the aforementioned recombinant adhesive protein where 6xAKPSYPPTYK or some amino acid sequences derived from MGFP-3A is attached to the carboxyl-terminus and/or amino-terminus of the MGFP-5, mussel adhesive protein.

The examples of the aforementioned nucleotide sequence encoding the above recombinant adhesive proteins are the nucleotide sequence shown in SEQ ID NO: 19, the nucleotide sequence shown in SEQ ID NO: 21, and the nucleotide sequence shown in SEQ ID NO: 23.

The present invention also provides a vector which contains an operably-linked nucleotide sequence encoding an adhesive protein.

The present invention also provides a transformant which contains an operably-linked a nucleotide sequence encoding an adhesive protein.

Another objective of the present invention is to provide a method for producing a mussel adhesive protein in a biologically active form in a large scale.

The present invention also provides a method of producing an adhesive protein which comprises the steps of:
(a) constructing a vector which contains an operably-linked nucleotide sequence encoding an adhesive protein;
(b) constructing a transformant by transforming a host cell with the aforementioned vector; and
(c) producing a recombinant adhesive protein by culturing the aforementioned transformant.

The present invention also provides a method of purifying an adhesive protein which comprises the steps of:
(a) lysing the transformant, and then centrifuging it to separate the supernatant and the pellet;
(b) making a suspension by adding an acidic organic solvent to the pellet; and
(c) centrifuging the suspension to separate the supernatant.

Another objective of the present invention is to provide an adhesive containing an adhesive protein as the active component.

The present invention also provides a method of adjusting the adhesive property of an adhesive comprising controlling the concentration of an adhesive protein which is an active component of the aforementioned adhesive, or treating the adhesive with one or more material selected from the group consisting of oxidant, filler and surfactant.

The present invention also provides a coating material containing an adhesive protein as an active component.

BRIEF DESCRIPTION OF THE DRAWINGS

FIGS. 7(A) to 7(C) show respectively (A) a photograph obtained by comparing the cell-growth of *E. coli* BL21/pMDG03 with the cell-growth of *E. coli* BL21/pTrcHis (*E. coli* BL21/pTrcHisA transformed with pTrcHisA) as time goes by, (B) a photography obtained by performing SDS-PAGE following Coomassie blue-staining, and (C) a photograph obtained by performing Western blot analyses of recombinant MGFP-3A MUTANT protein expression from *E. coli* BL21/pMDG03 and *E. coli* BL21/pTrcHis (*E. coli* BL21/pTrcHisA transformed with pTrcHisA) as time goes by.

FIGS. 20(A) to 20(F) are nucleotide sequences and amino acid sequences of the present invention as shown in SEQ ID Nos: 1 to 24.

DETAILED DESCRIPTION OF THE EMBODIMENTS

Figure 1:
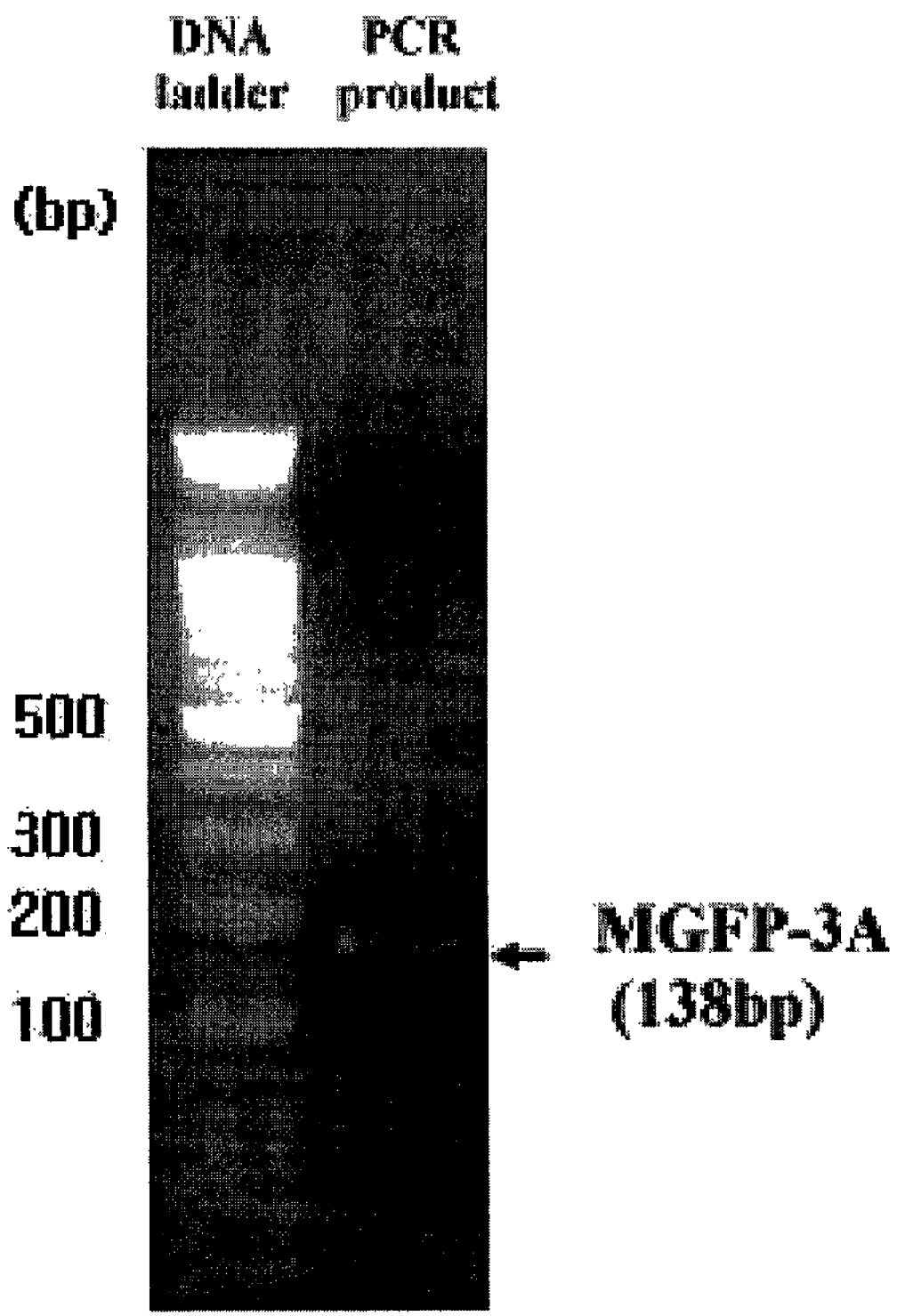
FIG. 1 is a photograph of the electrophoresis of MGFP-3A MUTANT protein cDNA fragments obtained by performing RT-PCR with template RNA extracted from *Mytilus galloprovincialis*.

The inventors of the present invention have constructed a gene encoding MGFP-3A MUTANT from a gene encoding an adhesion protein of MGFP-3A of *Mytilus galloprovincialis*, and have established an *E. coli* expression system for producing an adhesion protein translated from the gene.

They also established a recombinant adhesion protein that is a fusion protein of three or more mussel adhesion proteins, and a producing system therefore.

The adhesive protein of the present invention has the characteristic of attaching to a wide variety of substrates such as glass, metal, polymer resin, plastic or biological cell membranes such as prokaryotic membranes, eukaryotic membranes, and plant cell walls and lipids.

The adhesive protein of the present invention has at least 50% homology with the amino acid sequence shown in SEQ ID NO: 14, preferably 80%, more preferably 90%, and most preferably at least 95% homology, and at the same time can include amino acid sequences that have adhesive property, for example adhesive property that is similar to the amino acid sequence shown in SEQ ID NO: 14, or amino acid sequences that have 70 to 200% of the adhesive activity of the above.

For example, there is a protein that contains the amino acid sequence shown in SEQ ID NO: 14. An adhesive protein that contains the amino acid sequence as shown in the above SEQ ID NO: 14 is referred to as "MGFP-3A MUTANT" (*Mytilus galloprovincialis* foot protein type 3A Mutant) from hereon.

A nucleotide encoding MGFP-3A MUTANT can be indicated as a variety of nucleotide sequences depending on the amino acid codon usage, such as the nucleotide sequences shown in SEQ ID NO: 13.

Also, the adhesive protein of the present invention can further contain a peptide at the amino-terminus and/or carboxyl-terminus in order to improve the physicochemical properties of the adhesive protein. The above peptide may be added for the purpose of improving for example, the solubility, adhesion force, degree of crosslinking, and the degree of expression, purification, and recovery of protein. For example, the above peptide can be a general reporter protein such as GST or a histidine tag for the purpose of improving the purification.

The preferred examples of mussel adhesive proteins include MGFP-3A, FP-5, and an amino sequence with homology thereto.

The peptide preferably contains an amino acid sequence derived from an adhesive protein, and more preferably contains an amino acid sequence derived from a mussel adhesive protein. An example of the peptide is the amino acid sequence shown in SEQ ID NO: 25 repeated 1 to 10 times in tandem. In an embodiment of the present invention, a SEQ ID NO: 18 was constructed in which the amino acid sequence shown in SEQ ID NO: 25 is repeated 6 times in tandem, and attached to the amino- and/or carboxyl-terminus of the adhesive protein in the present invention. The amino acid sequence shown in the SEQ ID NO: 25 is a part of the sequence of the FP-1 protein.

Examples of recombinant adhesive proteins further comprising the amino acid sequence as shown in SEQ ID NO:25 are amino acid sequence shown in SEQ ID NO: 22, and amino acid sequence shown in SEQ ID NO:24. In addition, recombinant adhesive proteins including amino acid sequence shown in SEQ ID NO:14, amino acid sequence shown in SEQ ID NO:20, amino acid sequence shown in SEQ ID NO:22, or amino acid sequence shown in SEQ ID NO:24 can include histidine tag sequence attached to carboxyl-terminus and amino-terminus thereof in order to easily purify them. Furthermore, the GST tag can also be used to facilitate the purification and analysis.

The adhesive protein and recombinant adhesive protein of the present invention can be inserted into commonly used expression vectors constructed for expressing exogenous genes, and mass-produced through genetic engineering methods. The above vector may be selected according to the type and characteristics of the host cell used in the production of protein, or it may be newly constructed. Transforming the vector into the host cell and producing the recombinant protein from the transformant can easily be carried out through ordinarily employed methods. Selecting, constructing, transforming the vector and expressing the recombinant protein can be easily carried out by an ordinary person skilled in the art of the present invention, and partial variations in the ordinarily employed methods are also included in the present invention.

The sequence encoding an adhesive protein that is inserted into the vector is a sequence encoding an adhesive protein or a recombinant adhesive protein of the present invention, and is preferably selected from the group consisting of a nucleic acid encoding a protein that has at least 50% homology, preferably 80%, more preferably 90%, and most preferably at least 95% homology with the amino acid sequence shown in SEQ ID NOs: 20, 22, or 24, a nucleic acid encoding a protein that has at least 50% homology, preferably 80%, more preferably 90%, and most preferably at least 95% homology with the amino acid sequence shown in SEQ ID NO: 20, 22, or 24, where 6 histidine residues are additionally attached at the amino-terminus.

Figure 4:
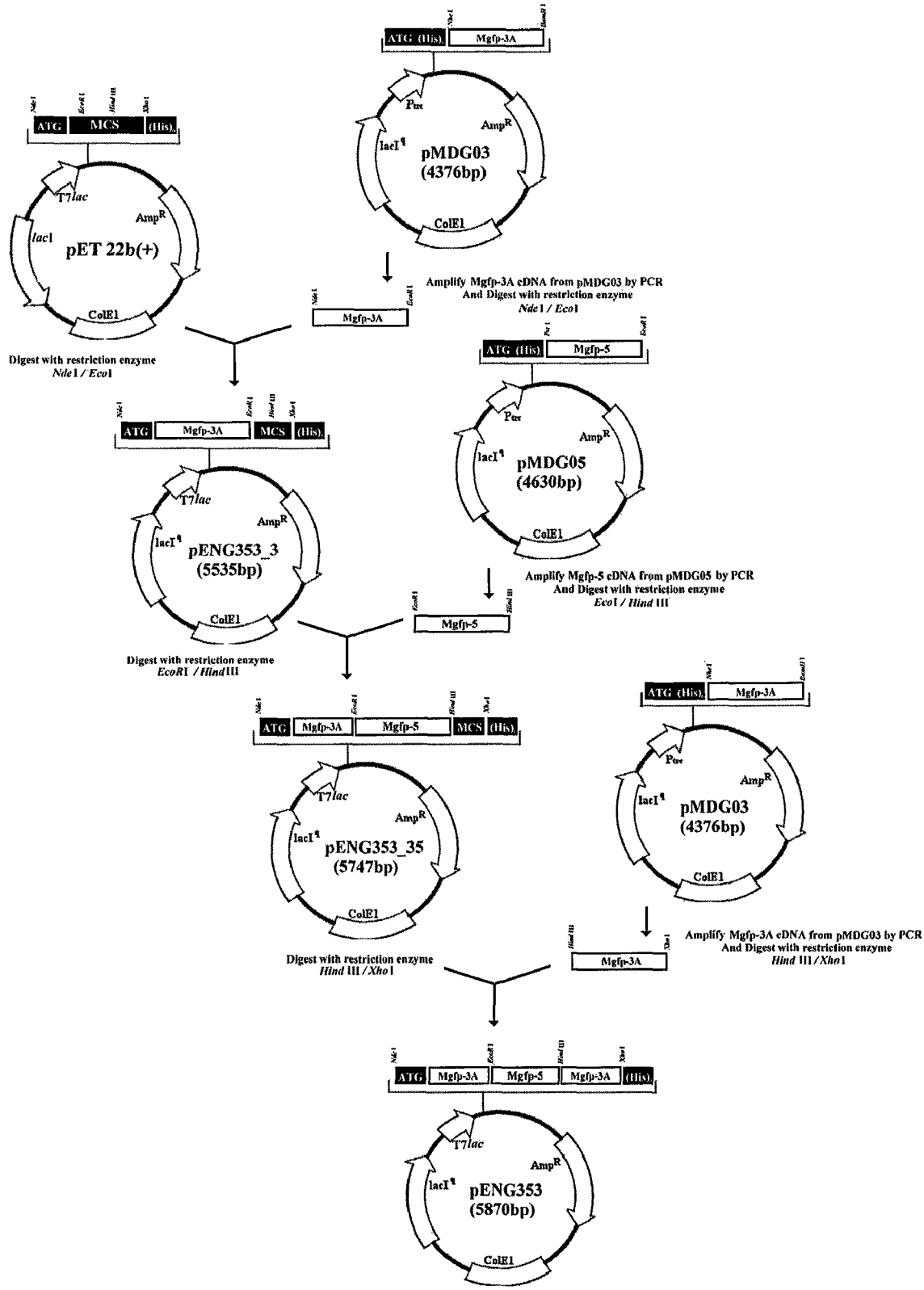
FIG. 4 is a schematic view showing the procedure for constructing the pENG353 vector for producing the recombinant MGFP-353 nucleotide sequence.
Figure 5:
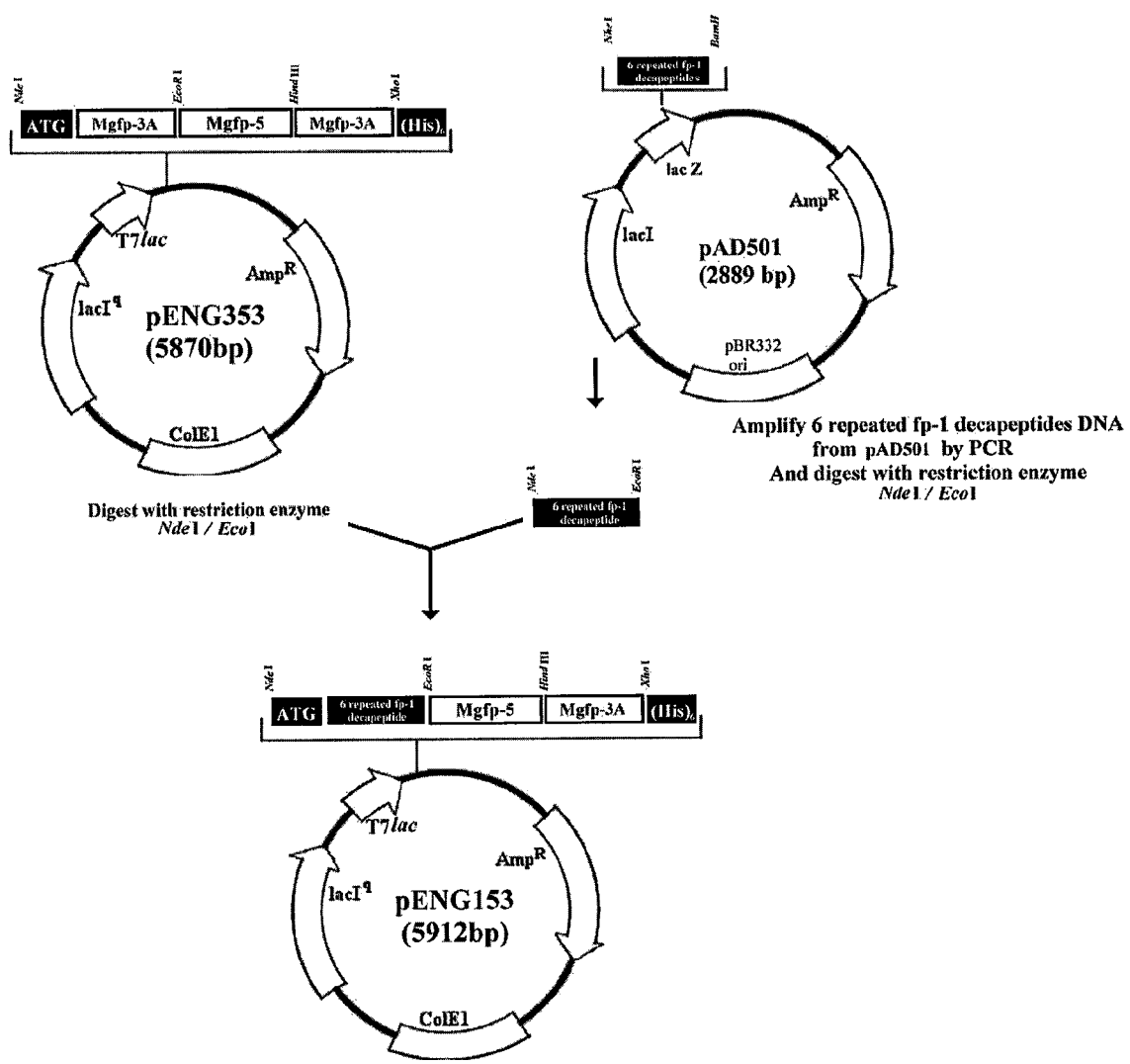
FIG. 5 is a schematic view showing the procedure for constructing the pENG153 vector for producing the recombinant MGFP-153 nucleotide sequence.
Figure 6:
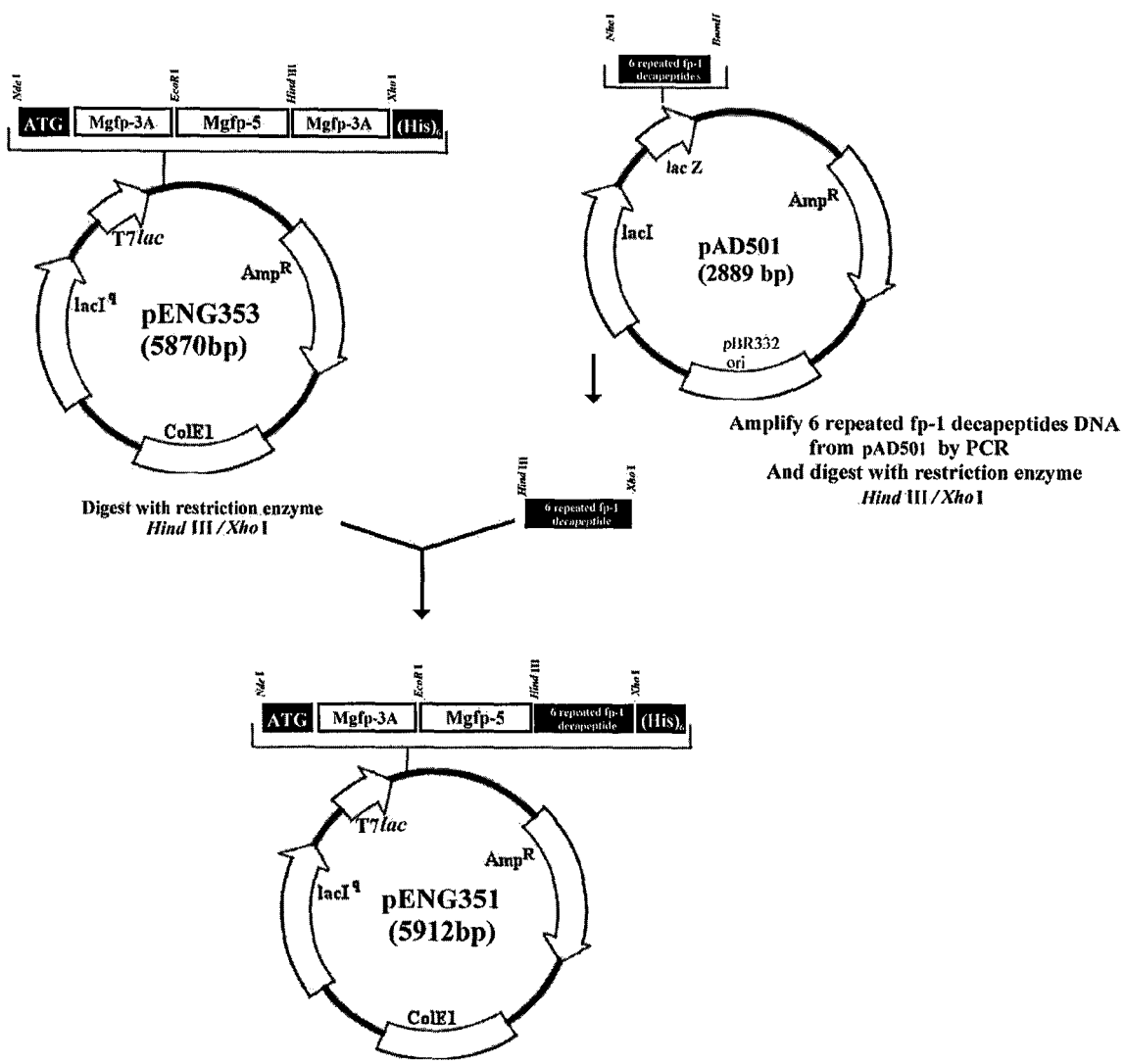
FIG. 6 is a schematic view showing the procedure for constructing the pENG153 vector for producing the recombinant MGFP-351 nucleotide sequence.

In an embodiment of the present invention, MGFP-3A MUTANT sequence shown in SEQ ID NO: 13) was cloned into a pTrcHis C vector and pMDG03 (FIG. 2) is constructed. The nucleotide sequence shown in SEQ ID NO: 17 is a gene encoding 6xAKPSYPPTYK which is 6 tandem repeats of the amino acid sequence shown in SEQ ID NO: 25), and is cloned into pUC18. Afterwards, the MGFP-5 sequence was cloned into a pTrcHisA vector to construct a pMDG05 vector (FIG. 4). Furthermore, in order to construct a vector that expresses a recombinant protein having a structure shown in Table 1 below, the sequences of MGFP-3A MUTANT, SEQ ID NO: 15 and SEQ ID NO: 17 were cloned into a pET-22(b) vector to construct pENG353, pENG153 and pENG 351 vectors (FIGS. 4, 5, 6).

TABLE 1

| Protein name | Structure (5' to 3') | Vector |
| --- | --- | --- |
| MGFP-353 | MGFP-3A MUTANT - MGFP-5 - MGFP-3A MUTANT | pENG353 |
| MGFP-153 | 6 x AKPSYPPTYK - MGFP-5 - MGFP-3A MUTANT | pENG153 |
| MGFP-351 | MGFP-3A MUTANT - MGFP-5 - 6 x AKPSYPPTYK | pENG351 |

The above pET vector is a widely known vector which contains a T7 promoter, which allows expression of exogenous protein by induction using IPTG(isopropylthio-β-D-galactoside), and which has 6 histidine sequences for protein purification by affinity chromatography at the 5' end of the exogenous gene in order to facilitate protein purification. In the present invention, the pMDG05 vector was deposited at the Korean Collection for Type Cultures (KCTC) at the Biological Resource Center of Korea located at Eouen-dong, Yuseong-gu, Daejon, Republic of Korea as of Jun. 20, 2002, and received an accession number of KCTC 10291BP. The pENG151 vector was deposited as of Jan. 19, 2005 and given an accession number of KCTC 10766BP.

The expression vector for the adhesive protein and recombinant adhesive protein can be transformed into a host cell selected from the group consisting of prokaryotes, eukaryotes, and eukaryote-derived cells, in order to construct a transformant. The prokaryote is selected from the group consisting of *E. coli* and *Bacillus*, the eukaryote is selected from the group consisting of yeast, insects, animals, and plants, and the eukaryote-derived cells are plant cells, insect cells, and animal cells, but is not limited thereto.

As an embodiment, pMDG03 was transformed into *E. coli* BL21 and pENG 353, pENG153 and pENG351 vectors were transformed into *E. coli* BL21(DE3) to construct *E. coli* BL21/pMDG03, *E. coli* BL21(DE3)/pENG 353, *E. coli* BL21(DE3)/pENG153 and *E. coli* BL21(DE3)/pENG351. The aforementioned 4 types of transformants can be cultured in typical LB media, and IPTG can be added to induce protein expression. The preferred method of expression of recombinant protein is to culture in LB media (5 g/liter yeast extract, 10 g/liter Tryptone, 10 g/liter NaCl), and adding 0.1 to 10 mM of IPTG when the optical density of the culture solution is 0.6 to 0.9 at 600 nm, then culturing for 2 to 7 hours.

The recombinant protein expressed in the above method is expressed in a water-soluble and/or insoluble form within the transformant, so the isolation and purification depends on how it is expressed. When it is expressed in a water-soluble form, the recombinant protein can be purified by running the disrupted cell supernatant through a chromatography column filled with an affinity resin such as a nickel resin. When it is expressed in a water-insoluble form, the recombinant protein can be purified by suspending the disrupted cell pellet in an acidic organic solvent, preferably an organic solvent with a pH of 1 to 6, then centrifuging the suspension to isolate the upper layer. Examples of the acidic organic solvent are acetic acid, citric acid, and lactic acid, but not limited thereto. The acetic acid used can be 5 to 30 (v/v) %, and preferably the cell pellet is dissolved in 20 to 30 (v/v) % acetic acid solution. The upper layer obtained through treatment with acidic organic solvent can further undergo gel filtration chromatography to further purify the recombinant protein.

According to the method of the present invention, 4 mg/L of the recombinant adhesive protein MGFP-3A MUTANT with at least 95% purity, about 38 mg/L of MGFP-353 of with at least 95% purity, about 36 mg/L of MGFP-153 with at least 95% purity, and about 44 mg/L of MGFP-351 of at least 95% purity can be obtained. While MGFP-353 has an adhesion force three times as high as that of MGFP-3A mutant, and one and a half times as high as MGFP-151, it has low modification efficiency of tyrosine residues due to a low solubility. Thus, MGFP-353 can be used for developing an excellent adhesive protein by improving solubility and concentration.

The adhesive protein and the recombinant adhesive protein obtained through its expression in the present invention have adhesive activity and can be used as adhesives. The adhesive activity was confirmed through the experiment of modifying the tyrosine residues in the protein to 3,4-dihydroxyphenyl-L-alanine (DOPA). Thus, the adhesive protein of the present invention can not only be used as an adhesive for a wide variety of substrates, but also be used as a bioadhesive since it is harmless to the human body.

The present invention also provides an adhesive that contains adhesive protein as an active component. The adhesive protein can be a form where 5 to 100% of its tyrosine residues are modified to DOPA, and the adhesive can additionally contain a substance that modifies the tyrosine residues in the protein to DOPA. A typical example of the above substance is tyrosinase, but is not limited thereto.

The above adhesive can further contain 0.5 to 90% by weight of an excipient that is generally contained in bioadhesives or is pharmaceutically acceptable. Examples of excipients include surfactants, oxidants, and fillers, but are not limited thereto (see: US Pat. Application Publication No. 2003-65060 and U.S. Pat. No. 5,015,677). The surfactant can be cationic, anionic, non-ionic, or amphoteric, where examples are sodium dodecylsulfate and sodium dodecylbenzensulfonate. The oxidant can be selected from the group consisting of tyrosinase, catechol oxidase, glutaraldehyde, formaldehyde, bis(sulfosuccinimidyl) suberate, 3,3'-Dithiobis(sulfosuccinimidyl propionate), $O_2$, $Fe^{3+}$, $H2O_2$ and $IO_4^-$ (see: Macromolecules 1998, 31, 4739-4745), and the filler can be selected from the group consisting of collagen, hyaluronic acid, condroitan sulfate, elastine, laminin, caseine, hydroxyapatite, albumin, fibronectin, and hybrin.

The adhesive of the present invention can be used to adhere or fix glass, plastic, polymer resin, or biological specimen, and the detailed mode and amount of usage, formulation and other such matters may follow Cell-Tak (BD Biosciences, Two Oak Park, Bedford, Mass., USA) which is currently available commercially. For example, the adhesive of the present invention can be a soluble, water-soluble, or insoluble formulation, and can be used in an amount of 0.01 to 100 ug/cm2 for a substrate but is not limited thereto. Furthermore, the mode of use follows the general mode of adhesive use, and the typical mode is coating.

The aforementioned biological specimen refers to any animal or plant categorized as a biological organism and any part derived from such animal or plant. For example, it refers to cells, tissues, organs, RNA, DNA, protein, peptide, polynucleotide, hormones, and compounds, but is not limited thereto.

Examples of application of the adhesive of the present invention are as follows, but not limited thereto: (1) adhesion of substrates under water (fresh or salt water); (2) orthopedic treatments such as treatment of bone, ligament, tendon, meniscus, and muscle, and implant of artificial materials; (3) treatment of perforations, lacerations, and cuts, and ophthalmic attachments such as corneal implants and artificial corneal implants; (4) dental attachments such as holding retainers, bridges, or crowns in place, securing loose teeth, repairing broken teeth, and holding fillers in place; (5) surgical treatments such as attachment of blood vessels, attachment of cellular tissue, artificial material implants, and closure of wounds; (6) plant attachments such as bonding of transplanted parts and wound healing; (7) drugs, hormones, biological factors, medications, physiological or metabolic monitoring equipment, antibiotics, and cell transplant (see: U.S. Pat. No. 5,015,677).

The present invention also provides a method of adjusting the adhesion force of the above adhesive by treating with a substance selected from the group consisting of surfactant, oxidant, and filler, or controlling the concentration of the adhesive protein which is an active component of the adhesive (see: U.S. Pat. No. 5,015,677). The surfactant, oxidant, and filler are the same as was described above.

The present invention also provides a coating agent which contains the above adhesive protein as an active component. Since the adhesive protein of the present invention has the characteristic of adhering to glass, plastic, polymer resin, or biological specimen, it can not only be used as a coating agent for these substrates, but also coat the surface of substrates that are used underwater to prevent oxidation of the substrates, since the adhesive protein is water-resistant and water-repellent. An example of application of the coating agent is to coat the motor propeller of ships to prevent corrosion, but is not limited thereto.

The above coating agent may consist solely of an adhesion protein, but can additionally contain commonly known adhesives, adhesive proteins other than the adhesive proteins of the present invention, resin contained in commonly known coating agents, organic solvents, surfactants, anticorrosive agents, or pigments. The content of the additional components may be appropriately adjusted within the commonly accepted range depending on the kind of component and formulation of the coating agent. Where an additional component is included, the adhesive protein as an active component is contained in the coating agent at a level that maintains the adhesive activity, and can for example be contained in the coating agent at 0.1 to 80% by weight.

The coating agent of the present invention can be manufactured in the form of cream, aerosol (spray), solid, liquid, or emulsion, but is not limited to these formulations.

Embodiments of the present invention are described below. The following embodiments are merely illustrative of the present invention and the present invention is not limited to the following embodiments.

In the following, the mussel used for cloning the MGFP-3A MUTANT, MGFP-5 gene was *Mytilus galloprovincialis*.

Example 1

Cloning of MGFP-3A MUTANT Gene

To perform PCR of MGFP-3A nucleotide sequence previously reported in Inoue, K. et al., 1999, Eur. J. Biochem. 239 1, 172-176 1996 for a gene encoding MGFP-3A MUTANT, MGFP-3A MUTANT-U, a primer shown in SEQ ID NO: 1 (5'-GGG GCT AGC GCT GAT TAT TAT GGT CCA AAG-3'), and MGFP-3A MUTANT-D, and a primer shown in SEQ ID NO:2 (5'-CCC GGA TCC TTA ATA ATA CTT TCG TCC-3') were constructed, and then used for reverse transcription reaction. A 138-bp PCR band of MGFP-3A MUTANT was obtained from cDNA library resulted from the reverse transcription as a template (FIG. 1), and inserted into pGEM-T (Promega, USA) of TA cloning vector for nucleotide sequence analysis.

As a result of the nucleotide sequence analysis, a coding sequence of adhesive protein with the exception of the secretion signal sequence of MGFP-3A MUTANT was obtained (SEQ ID NO:13). The amino acid sequence encoded by the nucleotide sequence is shown in SEQ ID NO: 14.

Example 2

Construction of Vector for Producing MGFP-3A MUTANT

Figure 2:
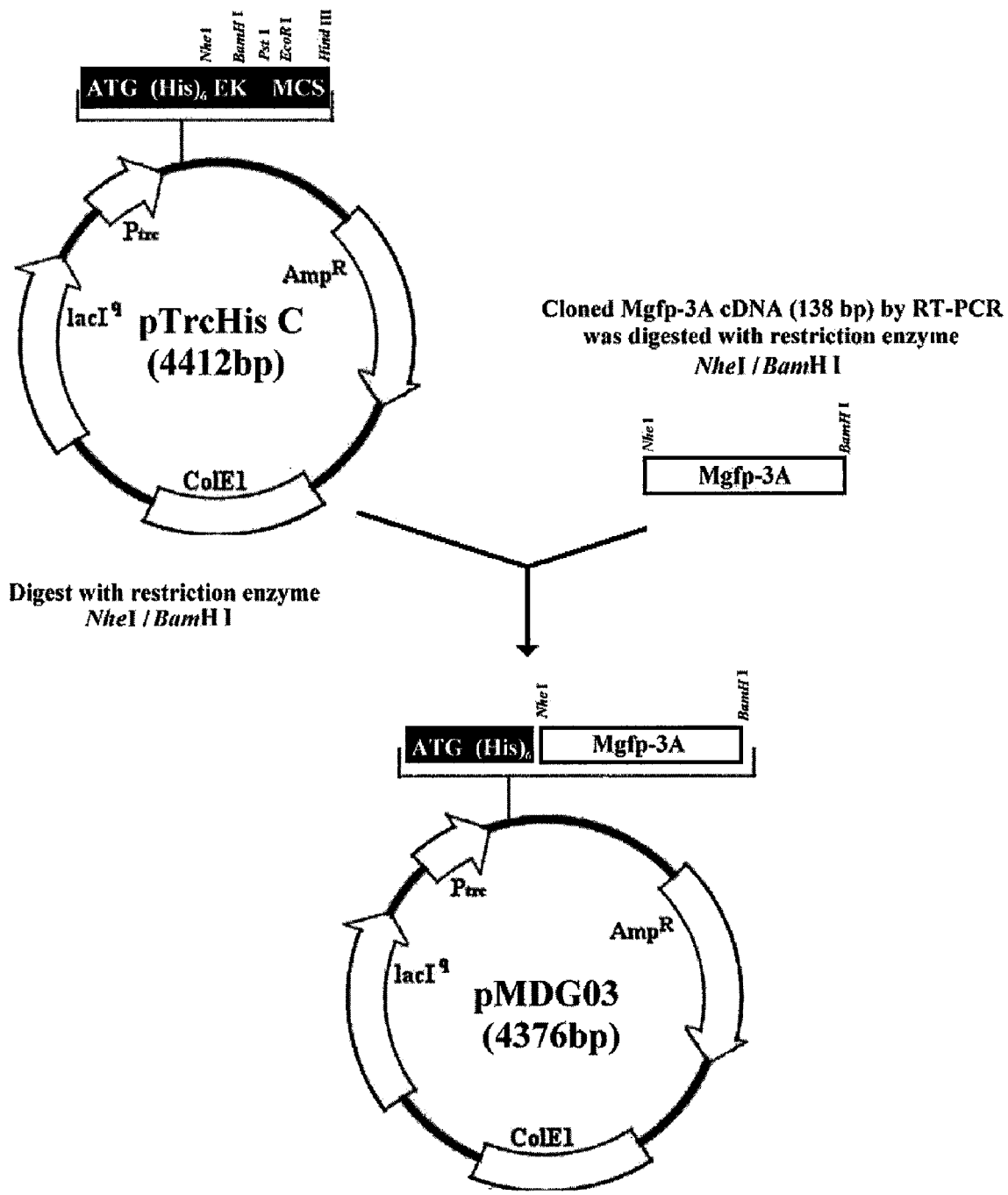
FIG. 2 is a schematic view showing the procedure for inserting MGFP-3A MUTANT cDNA into a pTrcHis vector to construct a pMDG03 vector.
Figure 3:
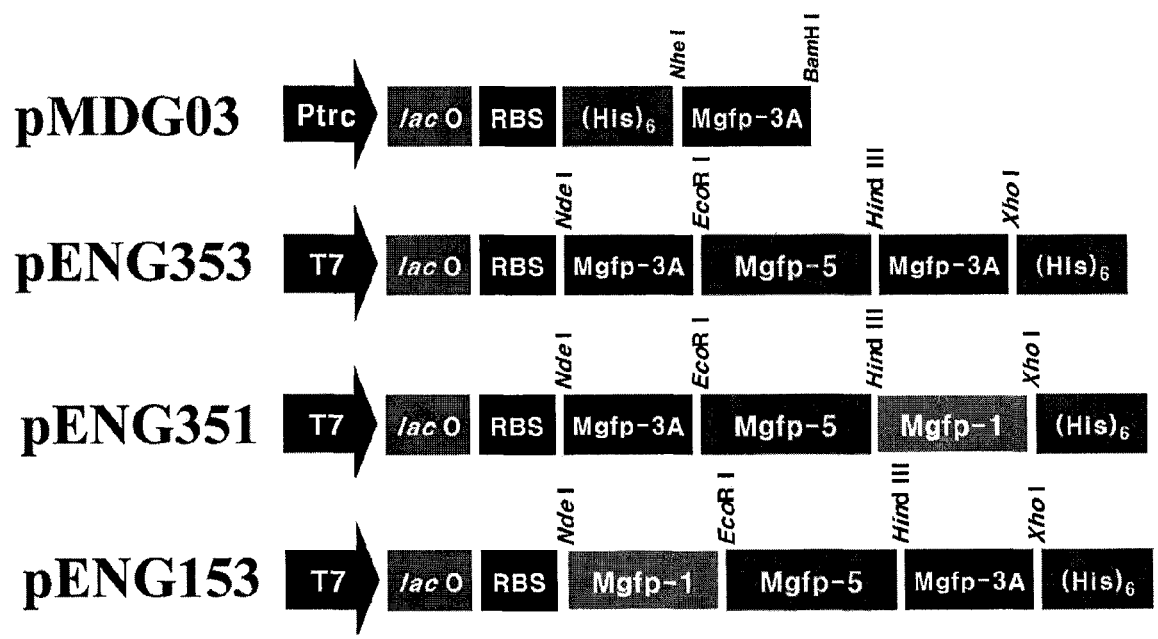
FIG. 3 shows vector diagrams of various combinations that can simultaneously express the MGFP-3A MUTANT, the 6xAKPSYPPTYK and the MGFP-5 gene.

The MGFP-3A MUTANT cDNA in pGEM-T vector was cut with restriction enzymes Nhe I and BamH I, and then inserted into pTrcHis-C vector (Invitrogen, USA) treated with Nhe I and BamH I. The obtained vector was named pMDG03 (4376 bp) (FIG. 2).

The pMDG03 vector contains an IPTG(isopropylthio-β-D-galactoside-inducible trc promoter which is widely used for *E. coli* expression system for inducing the expression with IPTG(Sigma, USA) and His6 tag sequence for separation and purification by affinity chromatography.

Example 3

Construction of a Vector Containing a Recombinant of FP-1, MGFP-3A MUTANT and MGFP-5

A vector for producing a recombinant mussel adhesive protein of MGFP-353 was named pENG353. A gene of MGFP-3A MUTANT contained in pMDG03 vector was amplified with a pair of primers ENG353F1 and ENG353R1, cut with Nde I and EcoR I, and inserted into pET-22b(+) (Novagen, USA), and treated with the same restriction enzymes to produce the pENG353_3 (5535 bp) vector. Then, a gene of MGFP-5 contained in pMDG05 vector was amplified with a pair of primers ENG353F2 and ENG353R2 which excluded the stop codon of MGFP-5 gene, cut with EcoR I and Hind III, and then inserted into pENG353_3 vector treated with Pst I and EcoR I to produce pENG353_35 (5747 bp). A gene of MGFP-3A MUTANT in pMDG03 was amplified with a pair of primer ENG353F3 and ENG353R3, cut with Hind III and Xho I, and then inserted into pENG353_35 vector treated with the same restriction enzymes to produce pENG353 vector (5870 bp) (FIG. 4).

By using the pENG353 vector, a vector pENG153 for producing a recombinant protein MGFP-153, and pENG351 vector for producing a protein MGFP-351 were prepared. The nucleotide encoding six repeat of deca-peptide AKPSYPP-TYK that is FP-1 model peptide was synthesized, and inserted into pUC18 vector to produce pAD501 according to the method of M. Kitamura, 1999, Journal of Polymer Science Part A: Polymer Chemistry 37, 729-736, except that the restriction enzyme site was changed from Nco I to Nhe I, and that six nucleotide sequence (TGATAG) located before second BamH I site were changed into five nucleotide sequence (ACTAT) to set the Open reading frame. The nucleotide sequence encoding FP-1 model peptide is shown in SEQ ID NO: 17.

The nucleotide sequence encoding FP-1 model peptide in pAD501 vector was amplified with a pair of primers (primers EGN153F and ENG153R) that included Nde I and EcoR I restriction enzyme sites, cut with Nde I and EcoR I, and inserted into pENG353 vector to produce pENG153 vector (FIG. 5). As described in the above, the nucleotide sequence encoding FP-1 model peptide in pAD501 vector was amplified with a pair of primers (primer ENG351F ध ENG351R) that included Hind III and Xho I restriction enzyme sites, cut with Hind III and Xho I, and inserted into pENG353 vector to produce pENG351 (FIG. 6).

pENG353, pENG153, and pENG351 vectors contains T7 promoter of *E. coli* expression system for mass production of protein, an IPTG-inducible lac operator for the induction of gene expression, and His6 tag sequence at the N-terminus for protein separation and purification with affinity chromatography.

Example 4

Construction and Cultivation of Transformant Producing MGFP-3A MUTANT and Recombinant Thereof The pMDG03 vector was introduced into *E. coli* cloning vector TOP10 (Invitrogen), and *E. coli* expression vector BL21 by making the host cells competent with CaCl$_2$ buffer, and heat shock method (left at 42° C., for 2 minutes). The transformed colony was selected with ampicillin (Sigma) to obtain *E. coli* Top10/pMDG3 and *E. coli* BL21/pMDG03. Unlike *E. coli* cloning vector TOP10 (Invitrogen) and *E. coli* expression vector BL21, pENG353, pENG153, and pENG351 were transformed and colony selection by using *E. coli* BL21 (DE3) (Novagen, USA). *E. coli* Top10/pENG353, Top10/pENG153, Top10/pENG351, *E. coli* BL21(DE3)/pENG353, *E. coli* BL21(DE3)/pENG153, and *E. coli* BL21 (DE3)/pENG351 were obtained.

BL21 strain transformed with pMDG03 vector, and BL21 (DE3) stain transformed with pENG353, pENG153, and pENG351 vector were incubated in LB (5 g/liter yeast extract, 10 g/liter Tryptone, 10 g/liter NaCl). To test the cultivation, the cell culture which was incubated in 50 mL sterilized tube containing 10 mL LB media and 500 μg ampicillin for 12 hours was inoculated into a 500 mL flask containing 100 mL LB media.

When absorbance of cell culture was about 0.8 at 600 nm wavelength, 1 mM IPTG as an inducer was added to the culture to induce expression of the recombinant proteins of MGFP-3A MUTANT, MGFP-353, MGFP-153, and MGFP-351.

Figure 7A:
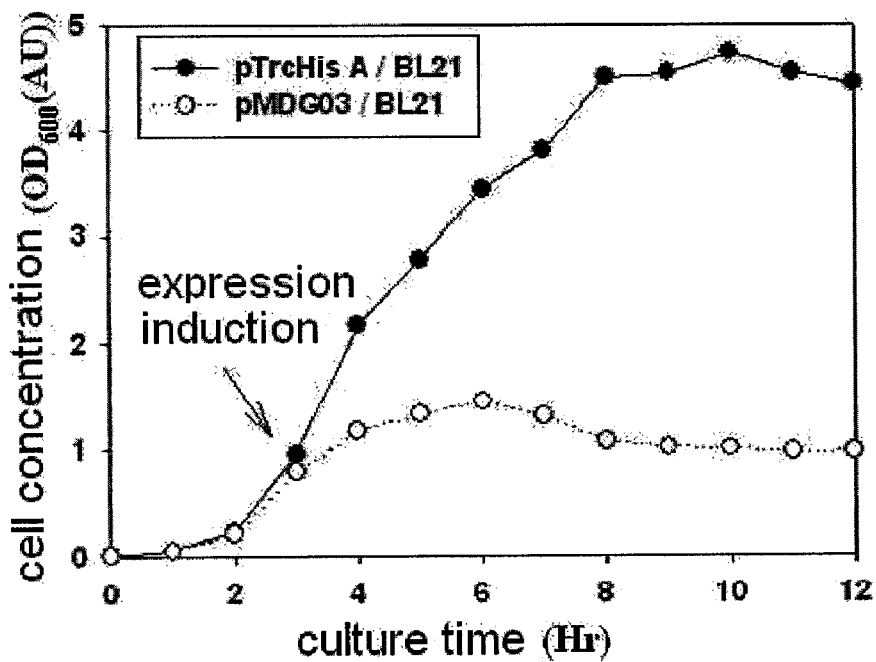
Figure 7B:
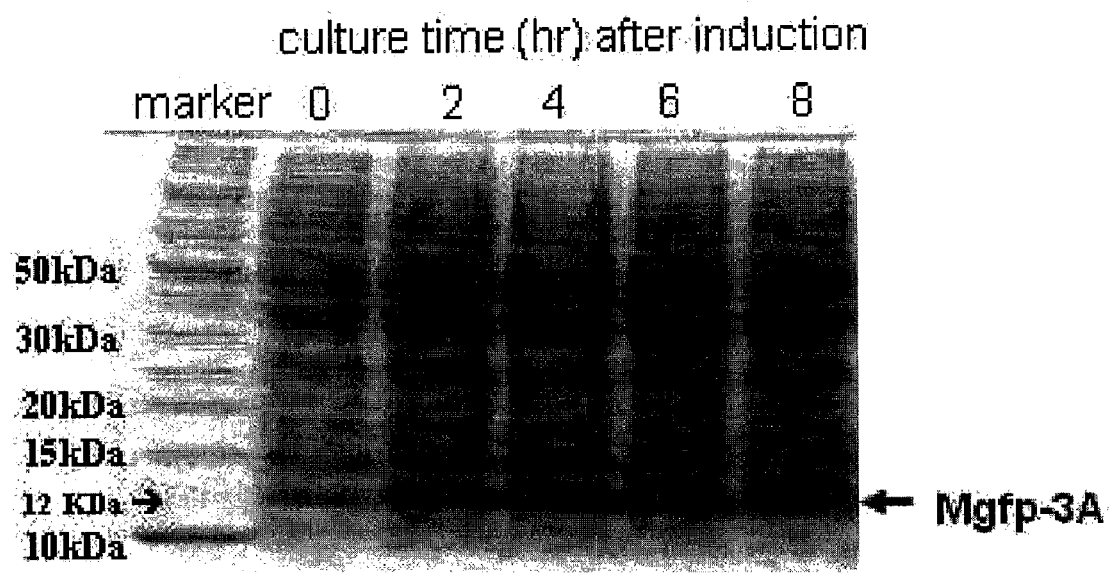
Figure 7C:
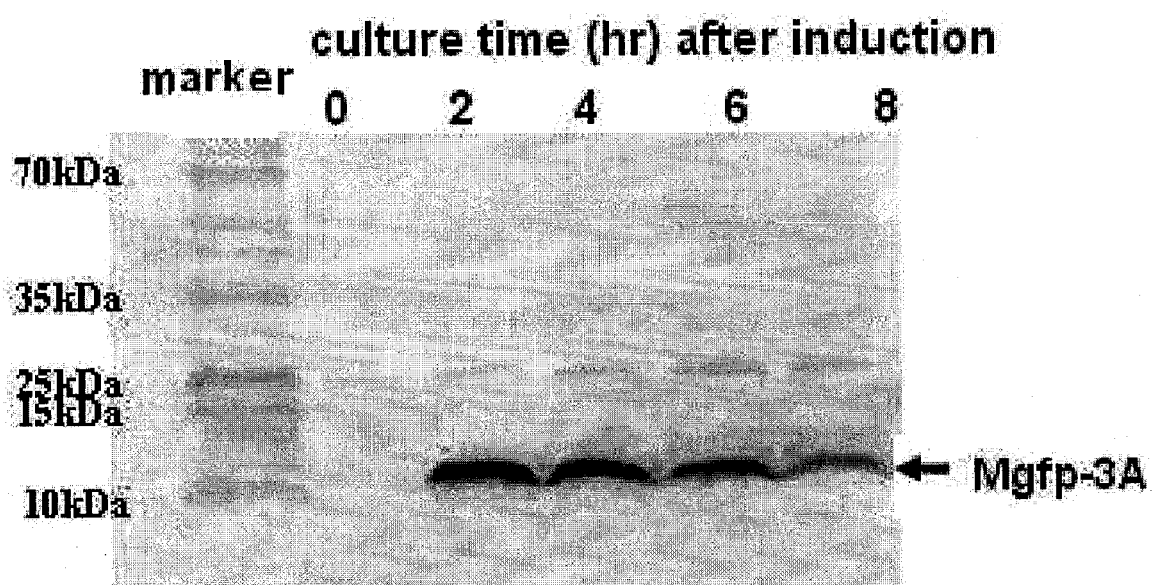

Compared with the culture of *E. coli* transformed with pTrcHis vector, the *E. coli* transformed with pMDG03 vector stopped growing shortly after expression induction (FIGS. 7A to 7C). Similar findings were confirmed when the transformant cell was cultivated with expression induced at different times (data not shown).

The expression of the recombinant adhesive proteins of MGFP-3A MUTANT inhibited cell growth. The reason for this is thought to be that the expressed adhesive proteins themselves damaged the cells or caused an imbalance in cell metabolism. In fact, an analysis of the amino acid sequences of the MGFP-3A MUTANT shows that glycine, arginine, asparagine, and tyrosine constitute about 60% of the amino acids. Thus, the expression of the adhesive protein can cause an imbalance of the amino acid usage.

Figure 8:
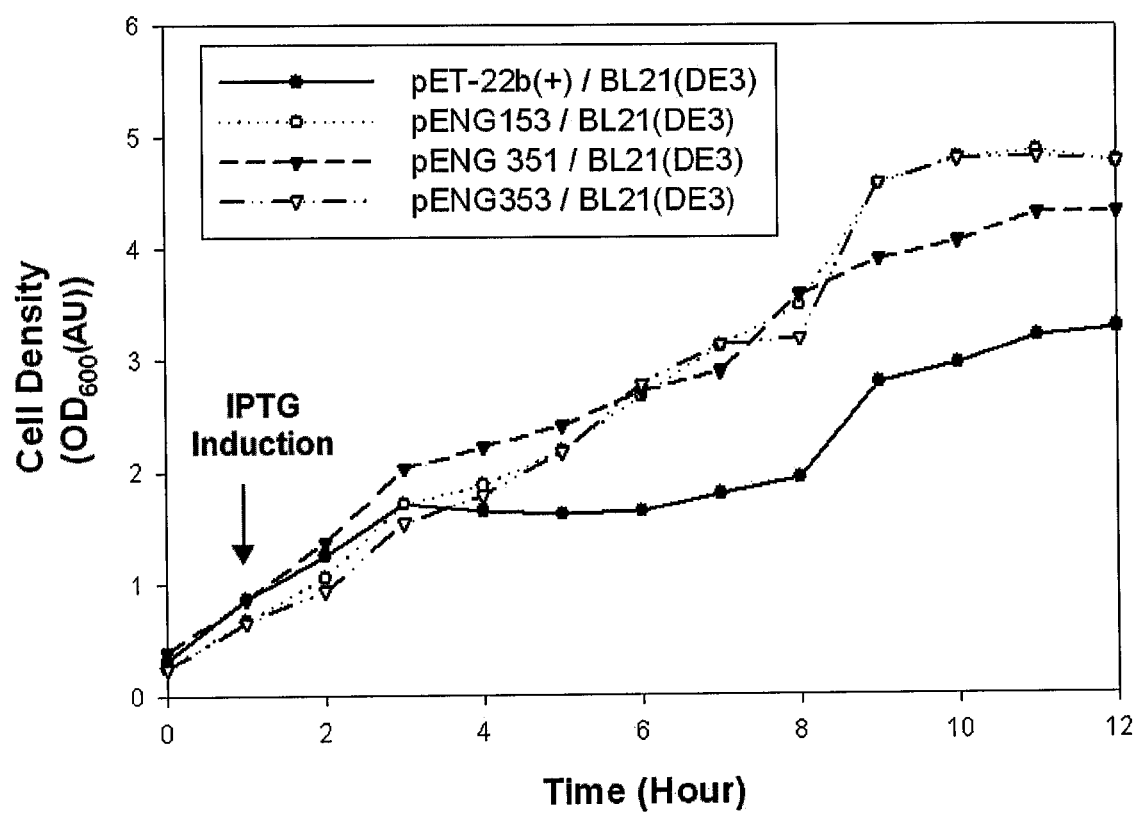
FIG. 8 is a graph measuring the cell-growth of *E. coli* BL21 (DE3) transformed with pET-22b(+), pENG353, pENG153, and pENG351, etc. with time

The transformant containing pMDG03 vector was deposited at the Korean Collection for Type Cultures (KCTC) at the Biological Resource Center of Korea located at Eouen-dong, Yuseong-gu, Daejon, Republic of Korea on Jan. 19, 2005, and received an accession number of KCTC 10765BP. Compared with pET-22b(+) transformant, the *E. coli* transformed with recombinant genes including MGFP-3A MUTANT, such as pENG353, pENG351, and pENG153 grew continuously after the protein expression was induced, unlike pMDG03 expression (FIG. 8)

Example 5

Expression and Purification of Recombinant MGFP-3A MUTANT Mussel Adhesive Protein The expression of the recombinant MGFP-3A MUTANT adhesive protein was analyzed with SDS-PAGE and Western blotting (FIG. 7A to 7C). 1 mL sample obtained from cell culture on every hour was centrifuged at 10000 rpm, at 4° C., for 10 minutes to remove the supernatant. Then, whole cell sample was stored at −80° C. for further analysis. Whole cell sample was suspended in 100 μl SDS-PAGE buffer (0.5M Tris-HCl (pH 6.8), 10% glycerol, 5% SDS, 5% β-mercaptoethanol, 0.25% bromophenol blue), and heated to 100° C. for 5 minutes. The sample was loaded on 15% SDS-PAGE and performed by electrophoresis to separate the proteins. The proteins were detected by Coomasie blue staining or silver staining (Bio-Rad, USA). The sample was loaded on 15% SDS-PAGE, electrophoresis was carried out and transferred onto nitrocellulose membrane at 15 V. The MGFP-3A MUTANT on nitrocelluose membrane was detected using monoclonal antibody for histidine affinity ligand (R&D systems, USA).

As the time passed after expression induction, the expression pattern of recombinant MGFP-3A MUTANT adhesive protein was analyzed with SDS-PAGE (FIG. 7B). Unlike the other proteins of *E. coli*, the recombinant MGFP-3A MUTANT adhesive protein was detected as a heavy band with size of about 12 kDa (about 3% of proteins in total). To investigate accurate band and expression pattern, Western blotting was performed (FIG. 7C). A heavy band on SDS-PAGE was recombinant MGFP-3A MUTANT adhesive protein. In considering the expression pattern with time, expression increased according to inducing time, reaching maximal expression 2 to 3 hours after induction, and then decreasing due to the degradation caused by protein cleavage enzymes.

Figure 9A:
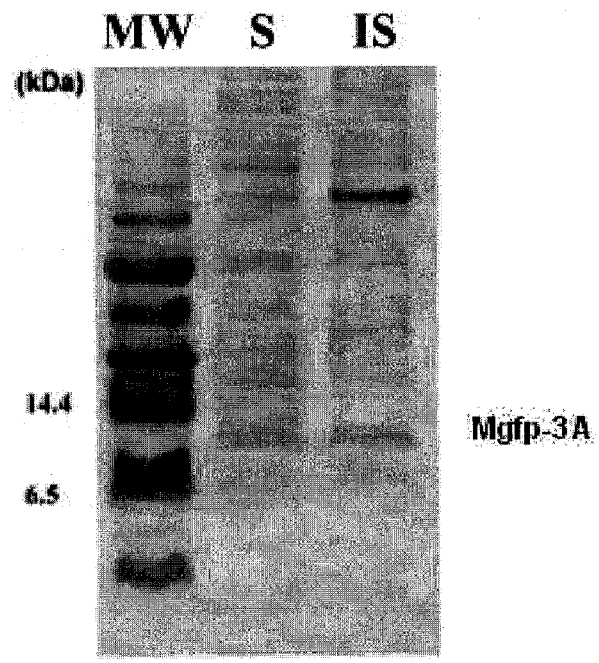
FIGS. 9(A) to 9(B) show respectively (A) a photograph obtained by performing SDS-PAGE followed by Coomassie blue-staining, and (B) a photograph obtained by performing Western blot analyses of soluble upper fraction (S) and insoluble cell debris fraction (IS) of the whole cell pellet isolated from *E. coli* BL21/pMDG03 culture solution.
Figure 9B:
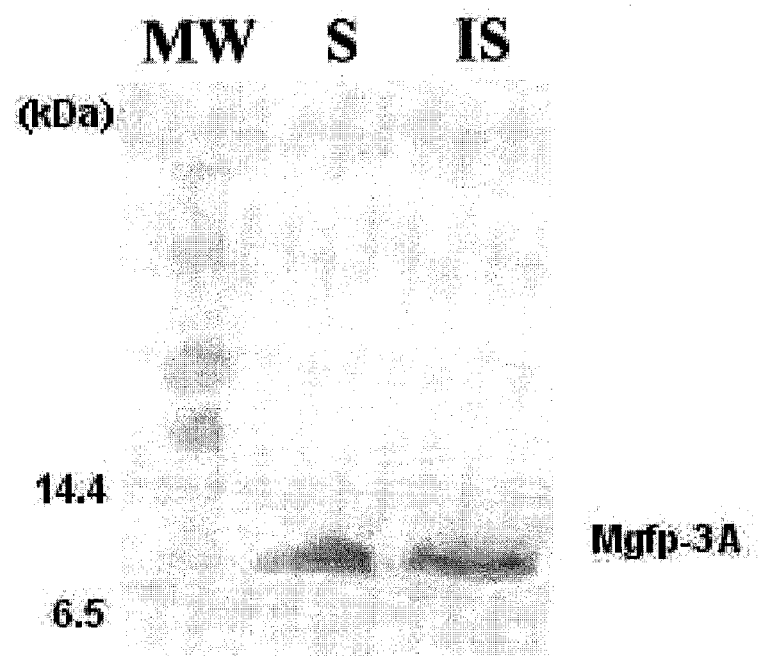

To further analyze recombinant MGFP-3A MUTANT adhesive protein expressed in *E. coli*, whole cell sample, and supernatant and cell debris which were obtained by sonication and separation were performed with SDS-PAGE (FIG. 9A) and Western blotting (FIG. 9B). In SDS-PAGE and Western blotting analysis, the supernatant and cell debris show a similar band of MGFP-3A MUTANT adhesive protein. Thus the MGFP-3A MUTANT adhesive protein has both water-insoluble and water-soluble characteristics.

To increase the separation and purification efficiency of the MGFP-3A MUTANT adhesive protein expressed in *E. coli*, affinity chromatography using histidine affinity ligand was carried out for the protein under modified conditions. Because the protein was expressed in *E. coli* cells, the cells were centrifuged, and suspended in a lysis buffer (8M urea, 10 mM Tris-Cl, 100 mM $NaH_2PO_4$, pH 8.0) for 1 hour at room temperature with shaking. The lysed cells were centrifuged at 14,000 rpm for 20 minutes to cell lysate, and the supernatant was obtained for further separation and purification. The affinity chromatography column was filled with 10 mL Ni-NTA™ Agarose (Qiagen) and 10 mL of 0.1 M NiSO4 (Samchun Chemicals). The separation and purification was performed with Acta Prime Purification System (Amersham Bioscience).

Figure 10A:
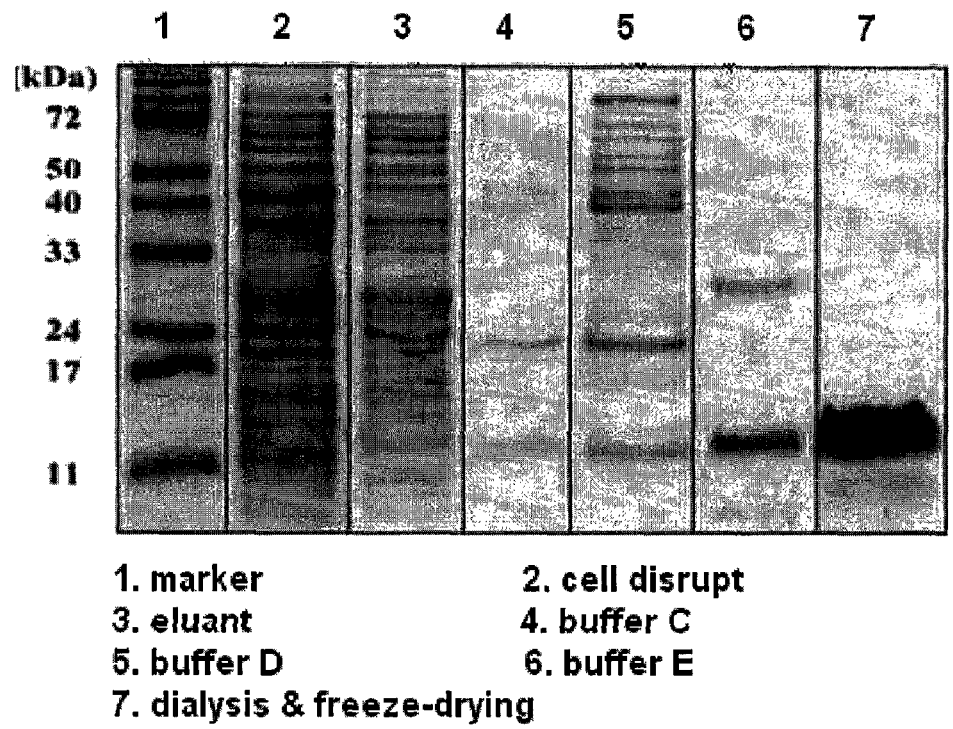
FIGS. 10(A) to 10(B) show respectively (A) a photograph obtained by performing SDS-PAGE followed by silver-staining and (B) a photograph obtained by performing Western blot analyses of eluted fractions obtained from affinity chromatograph purifying the recombinant MGFP-3A MUTANT protein from *E. coli* BL21/pMDG03.

Firstly, the column was equilibrated with 10 mL buffer B (8M urea, 10 mM Tris-Cl, 100 mM $NaH_2PO_4$, pH 8.0), and then loaded with 10 mL of cell supernatant. The column loaded with sample was sufficiently washed, eluted with 20 mL buffer C (8 M urea, 10 mM, Tris-Cl, 100 mM $NaH_2PO_4$, pH 6.3) and buffer D (8 M urea, 10 mM Tris-Cl, 100 mM $NaH_2PO_4$, pH 5.9) sequentially, and eluted with buffer E (8 M urea, 10 mM Tris-Cl, 100 mM $NaH_2PO_4$, pH 4.5) to obtain MGFP-3A MUTANT (FIG. 10A).

To remove urea contained in the purified sample in a high content, the purified sample was dialyzed (dialysis, Spectra/Por molecular porous membrane tubing, Spectrum Lab., USA) with 5% acetic acid buffer for 12 hours at 4° C. The resultant product was freeze-dried, and dissolved again to remove contaminants.

Figure 10B:
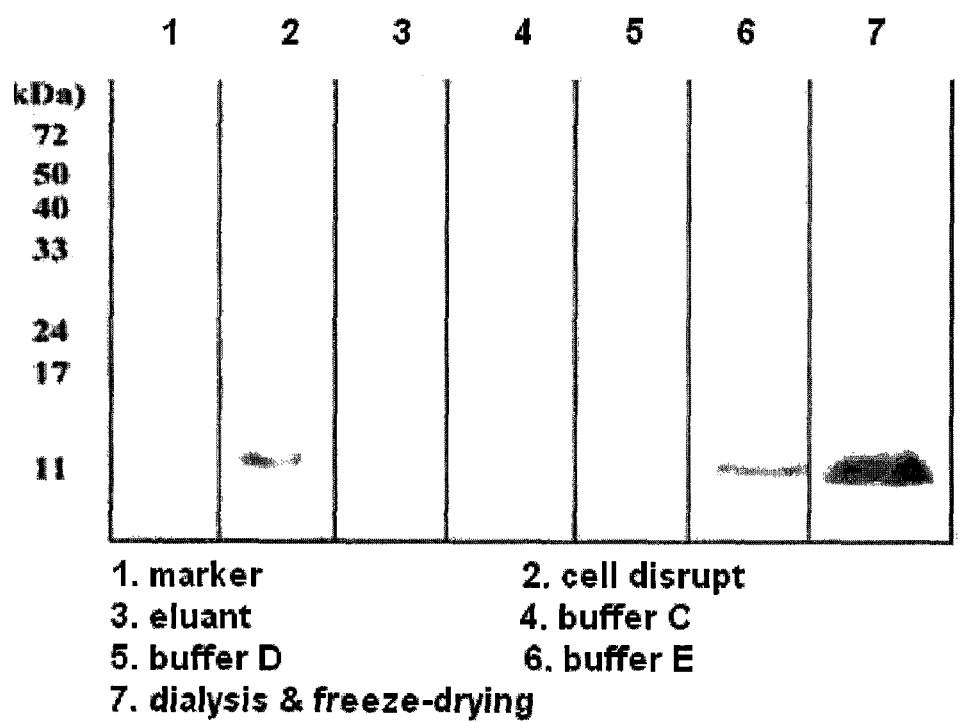

The purity and yield of purified recombinant MGFP-3A MUTANT adhesive protein were analyzed with SDS-PAGE and Western blotting (FIG. 10B). After performing affinity chromatography once, about 98.7% purity was achieved.

Figure 11:
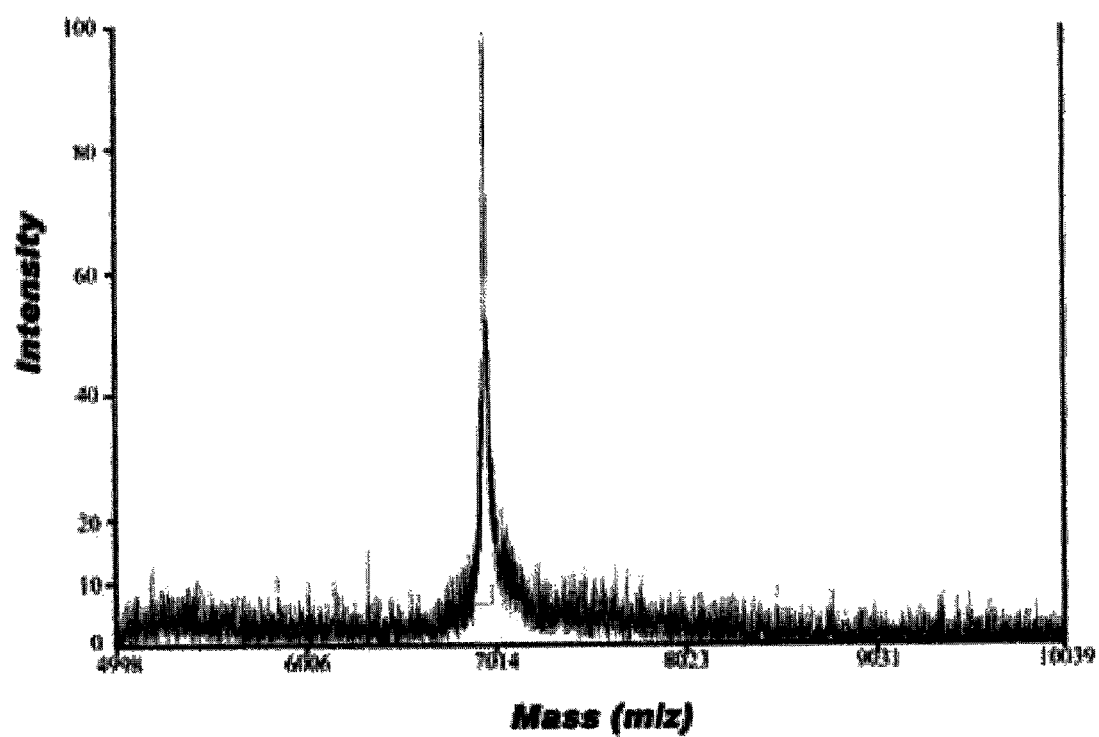
FIG. 11 is a mass spectrometry result of purified recombinant MGFP-3A MUTANT protein.

The mass analysis of recombinant MGFP-3A MUTANT protein was performed by MALDI-TOF (Matrix Assisted Laser Desorption Ionization-Time Of Flight) mass analyzer to produce the value of 7.09 kDa, which was consistent with the value calculated by amino acid sequence analysis (FIG. 11).

Example 6

Expression of MGFP-353 in *E. coli* BL21 (DE3)/pENG353

The expression of the recombinant MGFP-353 adhesive protein was analyzed with SDS-PAGE. 1 mL sample obtained from cell culture on every hour was centrifuged at 10000 rpm, at 4° C., for 10 minutes to remove the supernatant. Then, whole cell sample was stored at −80° C. for further analysis. Whole cell sample was suspended in 100 µl SDS-PAGE buffer (0.5M Tris-HCl (pH 6.8), 10% glycerol, 5% SDS, 5% β-mercaptoethanol, 0.25% bromophenol blue), and heated to 100° C. for 5 minutes. The sample was loaded on 15% SDS-PAGE and performed by electrophoresis to separate the proteins. The proteins were detected by Coomassie blue staining (Bio-Rad, USA).

Figure 12A:
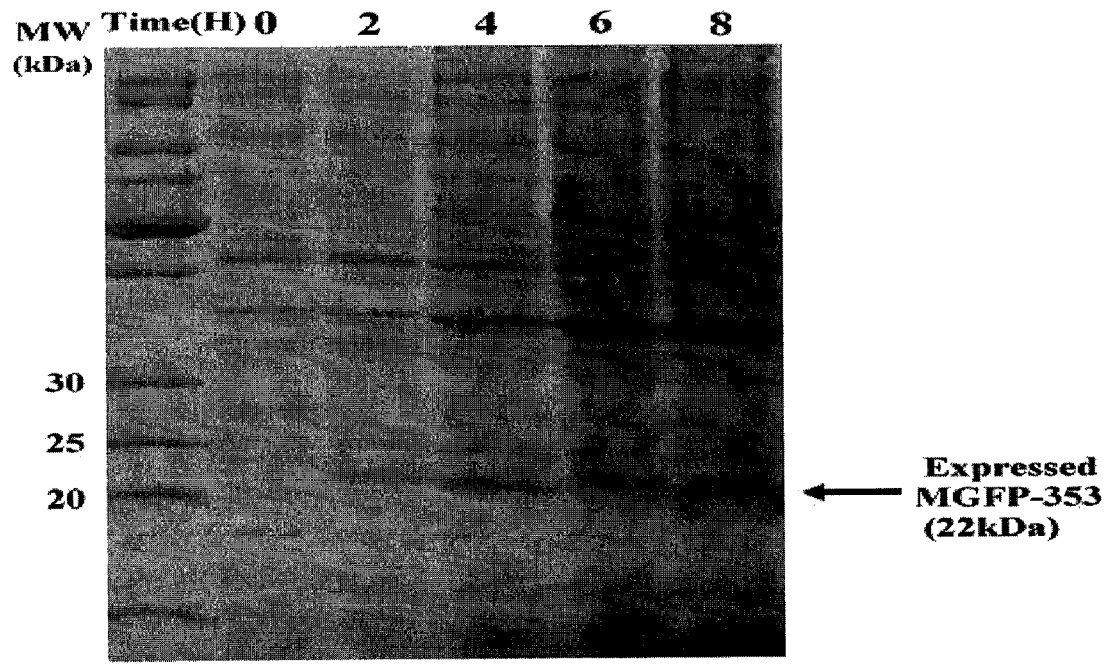
FIGS. 12(A) to 12(B) show respectively (A) a photograph obtained by performing SDS-PAGE followed by silver-staining to show expression level of a recombinant MGFP-353 protein from *E. coli* BL21(DE3)/pENG353 with time, and (B) a photograph obtained by performing SDS-PAGE to show the intracellular solubility of the expressed MGFP-353.
Figure 12B:
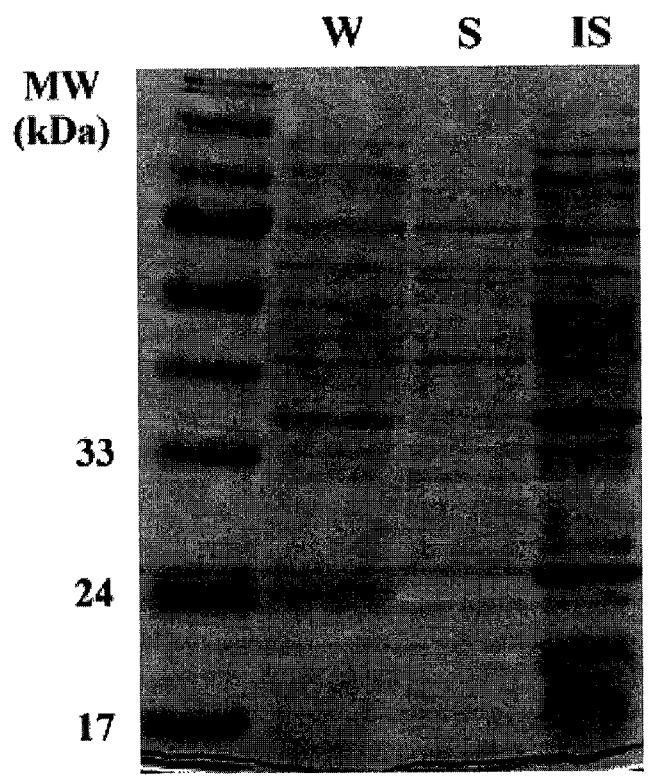

As the time passed after expression induction, the expression pattern of recombinant MGFP-3A MUTANT adhesive protein was analyzed with SDS-PAGE (FIG. 12A). Unlike the other proteins of *E. coli*, the recombinant MGFP-353 adhesive protein was detected to express a heavy band having a size of about 22 kDa. The heavy band on SDS-PAGE was recombinant MGFP-3A MUTANT adhesive protein. In considering the expression pattern with time, the expression increased continuously after expression induction To further analyze recombinant MGFP-353 adhesive protein expressed in *E. coli*, whole cell sample, and supernatant and cell debris which were obtained by sonication and separation were performed with SDS-PAGE (FIG. 12B). In the SDS-PAGE analysis, only the cell debris showed the band of MGFP-353 adhesive protein. Thus, the MGFP-353 adhesive protein is a water-insoluble inclusion body.

To increase the separation and purification efficiency of the water-insoluble MGFP-353 adhesive protein expressed in *E. coli*, affinity chromatography using histidine affinity ligand was performed under modified conditions. Because the protein was expressed in an inclusion body in the *E. coli* cell, the cell was centrifuged, and suspended in a lysing buffer A (6M GuHCl, 100 mM NaH$_2$PO$_4$, mM Tris.Cl, pH 8.0) for 1 hour at room temperature with shaking. The disrupted cell was centrifuged at 14,000 rpm for 20 minutes to cell lysate, and the supernatant was obtained for further separation and purification. The affinity chromatography column was filled with 10 mL Ni-NTA™ Agarose (Qiagen) and 10 mL of 0.1 M NiSO$_4$ (Samchun Chemicals). The separation and purification was performed with Acta Prime Purification System (Amersham Bioscience).

Firstly, the column was equilibrated with 10 mL buffer (6M GuHCl, 100 mM NaH$_2$PO$_4$, 10 mM Tirs.Cl, pH 8.0), and then loaded with 10 mL of cell supernatant. The column loaded with sample was sufficiently washed with buffer A, eluted with 20 mL buffer C (8 M Urea, 10 mM Tris-Cl, 100 mM NaH$_2$PO$_4$, pH 6.3) and buffer D (8 M Urea, 10 mM Tris-Cl, 100 mM NaH$_2$PO$_4$, pH 5.9) sequentially, and eluted with buffer E (8 M urea, 10 mM Tris-Cl, 100 mM sodium phosphate, pH 4.5) to obtain MGFP-353 (FIG. 15A).

To remove urea contained in the purified sample in a high content, the purified sample was dialyzed (dialysis, Spectra/Por molecularporous membrane tubing, Spectrum Lab., USA) with 5% acetic acid buffer for 12 hours at 4° C. The resultant product was freeze-dried, and dissolved again to remove contaminants.

Figure 15A:
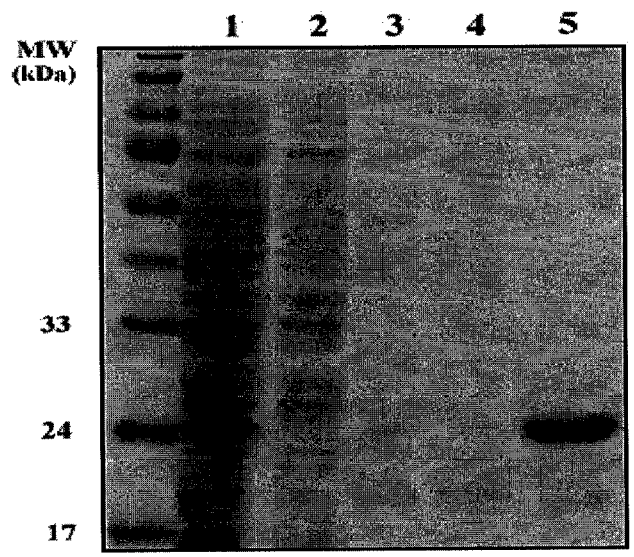
FIGS. 15(A) to 15(C) are photographs of silver-stained SDS-PAGE analysis of each MGFP-353(A), MGFP-153(B), and MGFP-351(C) which are obtained by chromatography.

The purity and yield of purified recombinant MGFP-353 adhesive protein were analyzed with SDS-PAGE and Coomassie blue-staining (FIG. 15A). After performing affinity chromatography once, about 95% or higher purity was achieved.

Because the recombinant MGFP-353 formed an inclusion body in the cell, separation with chromatography was applied to the inclusion body [Jan-Christer J., Protein Expression and Purification. 25: 174-179 (2002)], thereby increasing the purification efficiency.

Example 7

Expression and Purification of MGFP-153 in *E. coli* BL21(DE3)/pENG153

In accordance with the same method of Example 6, *E. coli* BL21(DE3)/pENG153 was incubated, and cell pellets were collected. Then, the water-insoluble fraction and the water-soluble fraction were obtained. The SDS-PAGE was performed on the sample. Unlike the other proteins of *E. coli*, the recombinant MGFP-153 adhesive protein was detected to express a heavy band having a size of about 24 kDa.

Figure 13A:
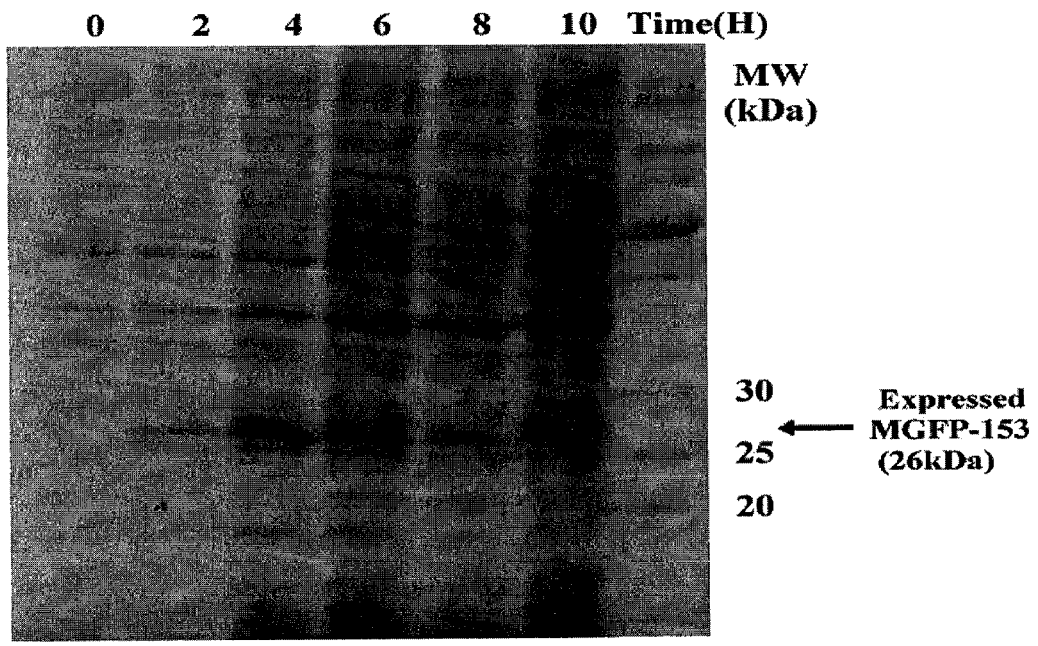
FIGS. 13(A) to 13(B) show respectively (A) a photograph of silver-stained SDS-PAGE analysis of a recombinant MGFP-153 protein expression level with *E. coli* BL21(DE3)/pENG153 in time and (B) a photograph of Western blot analysis of intracellular solubility of MGFP-153.
Figure 13B:
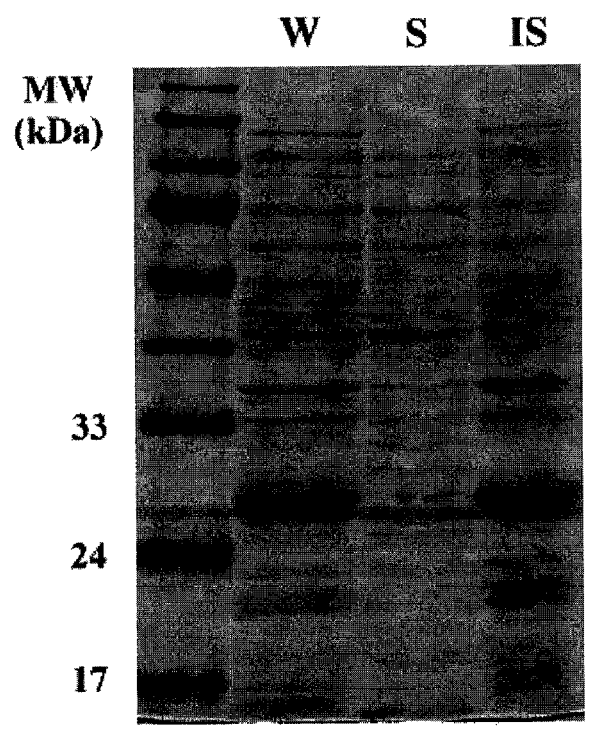

FIG. 13A to 13B are photographs of SDS-PAGE analyzing the expression of recombinant adhesive protein MGFP-153 in *E. coli* L21(DE3)/pENG153. W is cell pellet, S is water-soluble supernatant, and IS is water-insoluble cell debris. FIG. 13 suggests that the recombinant protein MGFP-153 was expressed as intracellular water-insoluble aggregate. MGFP-153 which was expressed as intracellular water-insoluble aggregate in *E. coli* was purified according to the method of Example 6 (FIG. 13B).

Example 8

Expression and Purification of MGFP-351 in *E. coli* BL21(DE3)/pENG351

In accordance with the same method of Example 6, *E. coli* BL21(DE3)/pENG351 was incubated, and cell pellets were collected. Then, the water-insoluble fraction and the water-soluble fraction were obtained. SDS-PAGE was performed on the sample. Unlike the other proteins of *E. coli*, the recombinant MGFP-153 adhesive protein was detected to express a heavy band having a size of about 24 kDa.

Figure 14A:
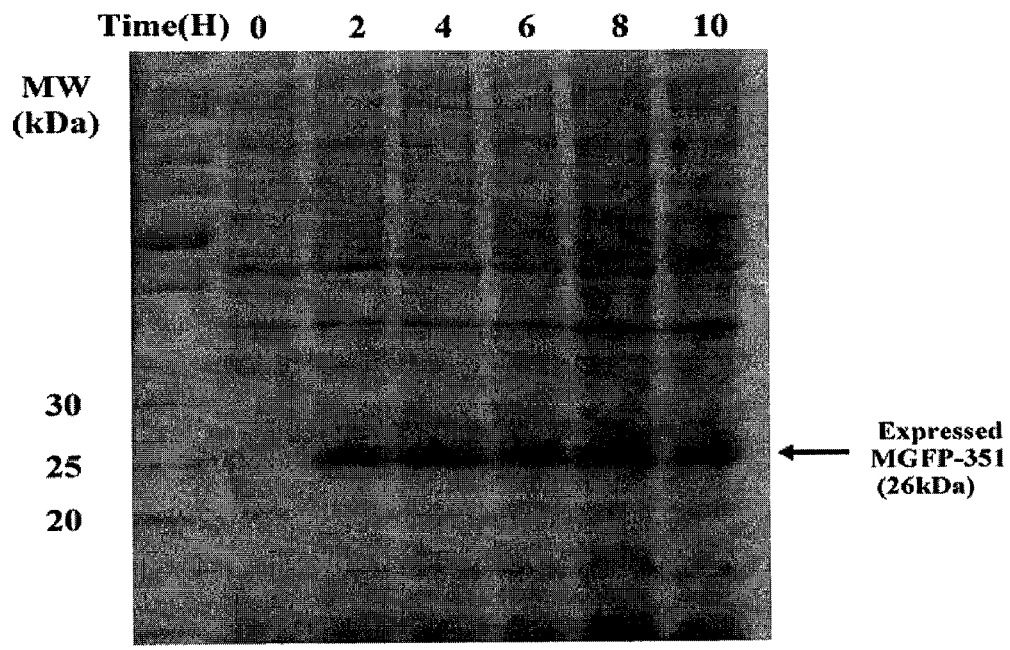
FIGS. 14(A) to 14(B) show respectively (A) a photograph of silver-stained SDS-PAGE analysis of a recombinant MGFP-351 protein expression level with *E. coli* BL21(DE3)/pENG351 in time and (B) a photograph of Western blot analysis of intracellular solubility of MGFP-351.
Figure 14B:
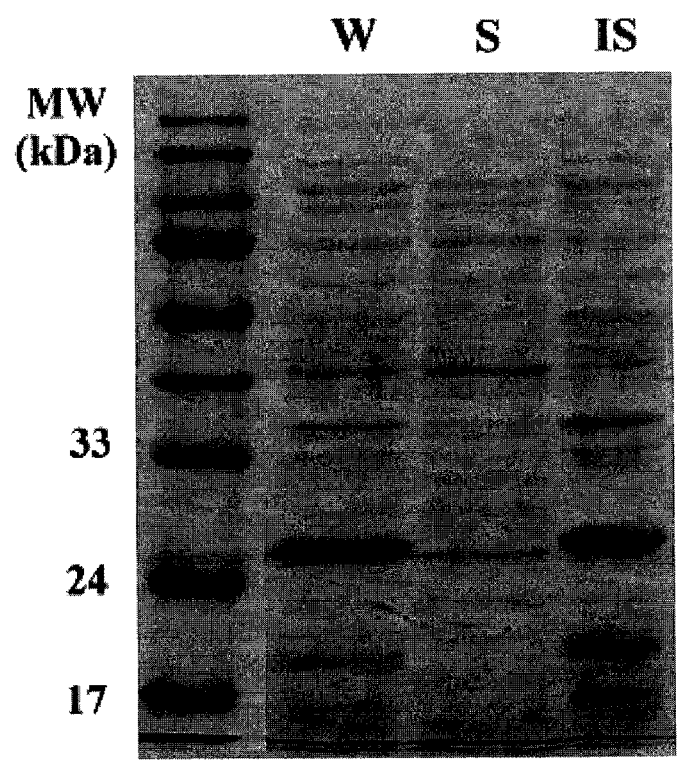
Figure 15B:
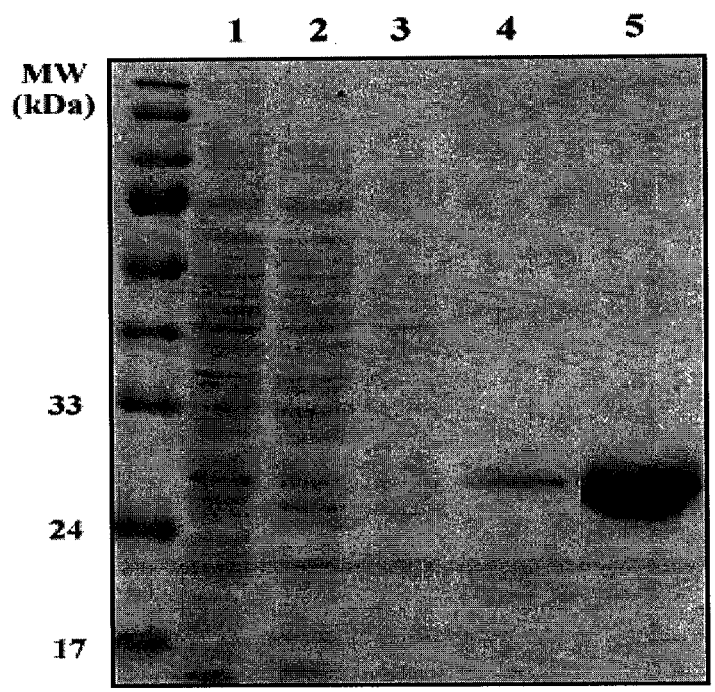
Figure 15C:
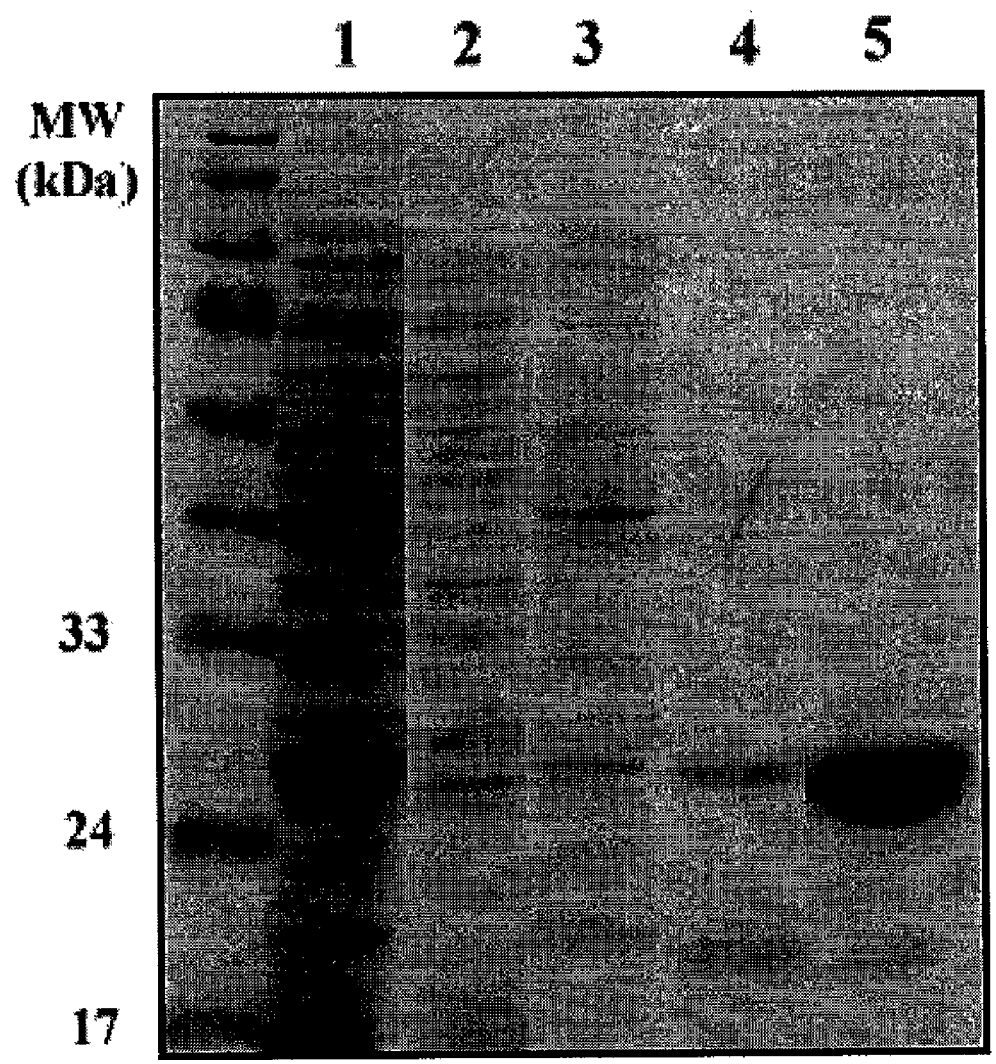

FIG. 14 shows a photograph of SDS-PAGE of analyzing the expression of recombinant adhesive protein MGFP-351 in *E. coli* BL21(DE3)/pENG351. MW is a size marker, W is cell pellet, S is water-soluble supernatant, and IS is water-insoluble cell debris. FIG. 14 suggested that the recombinant protein MGFP-351 was expressed intracellular water-insoluble aggregate. MGFP-351 which was expressed in intracellular water-insoluble aggregate in *E. coli* was purified according to the method of Example 6 (FIG. 15B).

Example 9

Chemical Modification of Tyrosine Residues

The tyrosine residues in the amino acids of mussel adhesive protein were modified to DOPA residues and finally DOPA-quinone residues by chemical modification. It has been reported that the modified DOPA and DOPA-quinone are very much responsible for adhesion on a surface. The recombinant mussel adhesive proteins were chemically modified with tyrosinase derived from a mushroom. The purified MGFP-3A MUTANT, MGFP-353, MGFP-153 and MGFP-351 were dissolved in 5% acetic acid buffer and adjusted to 1.44 mg/mL of protein concentration using a Bradford assay. All proteins were modified with 10 unit/mL tyrosinase (Sigma) at 25° C. for 6 hours with shaking.

Example 10

Measurement of Adsorption of Recombinant Adhesive Protein, MGFP-3A MUTANT using QCM (Quartz Crystal Microbalance)

The quartz crystal used (Seiko EG & G) was a gold-coated AT-cut quartz 5 mm in diameter with a basic resonant frequency of 9 MHz. A 5 µl drop of a 1.44 mg/mL protein solution (BSA, Cell-Tak and recombinant MGFP-03 protein) was each placed onto the gold surface of the quartz crystal and kept at 25° C. in a constant-temperature water bath for 1 hour.

After taking it out of the water bath and drying, the gold surface was rinsed thoroughly in double distilled water for 1 h with shaking and the water remaining on the quartz crystal was evaporated using a vacuum pump. Dried quartz crystal was connected to an EQCM controller (QCA917; Seiko EG & G) and variations in resonance frequency were measured. Since the resonance frequency of the quartz crystal decreases as a function of increase in the mass adsorbed on its surface (G. Sauerbrey, 1959, Z. Phys, 155, 206), the increase in mass was calculated by Equation 1 (M. Thomson, 1991, Analyst, 116, 881-889) with the value for change in resonance frequency.

$$\Delta mass = \frac{-\Delta freq \times A \times \sqrt{\mu_q \times \rho_q}}{2 \times F_q^2} \quad \text{(equation 1)}$$

In the above Equation 1, $\Delta mass$ is change in mass, $\Delta freq$ is change in resonance frequency, $\mu q$ is AT-cut quartz crystal constant ($2.947 \times 1.011$ g/cm/sec$^2$), Pq is the quartz crystal density (2.648 g/cm$^2$), Fq2 is reference frequency (9.00 MHz), and A is quartz crystal surface area (0.196 cm$^2$).

Figure 16:
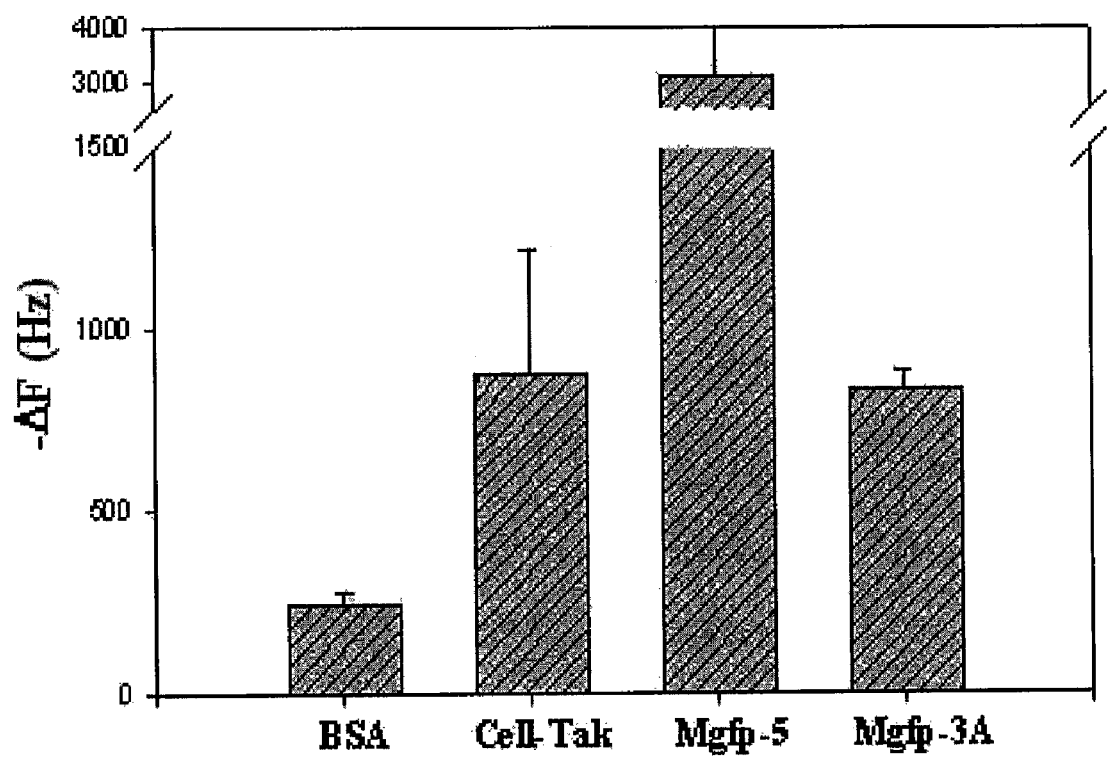
FIG. 16 is a result from QCM analysis showing as a frequency change the amount of adsorption on gold surface by adsorption properties of modified versions of BSA, Cell-Tak, MGFP-5, and MGFP-3A which are treated with tyrosinase.

FIG. 16 is the result of QCM analysis of BSA, Cell-Tak and recombinant MGFP-3A MUTANT protein where the tyrosines were treated, showing the level of adsorption onto the gold surface as change in frequency.

The adhesion force of recombinant MGFP-3A MUTANT was lower than that of recombinant MGFP-5 but similar to that of Cell-Tak, the commercially available, naturally extracted mussel adhesive protein product.

Example 11

Measurement of Adhesion Force of Recombinant Adhesion Protein Using AFM (Atomic Force Microscopy)

The force-distance curve was obtained using AFM (SPA400; Seiko Instruments), and AFM cantilevers were done according to the technique of Ducker et al. [W. Ducker, Nature, 1991, 353, 239-241] (FIG. 20). The spring constant of the cantilevers (Veeco & Seiko Instruments) used for the present experiments was 11 N/m. A glass bead (Park Science) of 20 µm diameter was attached to the tip of the cantilever using an epoxy resin (Vantico), and kept at room temperature for 24 h.

Figure 17:
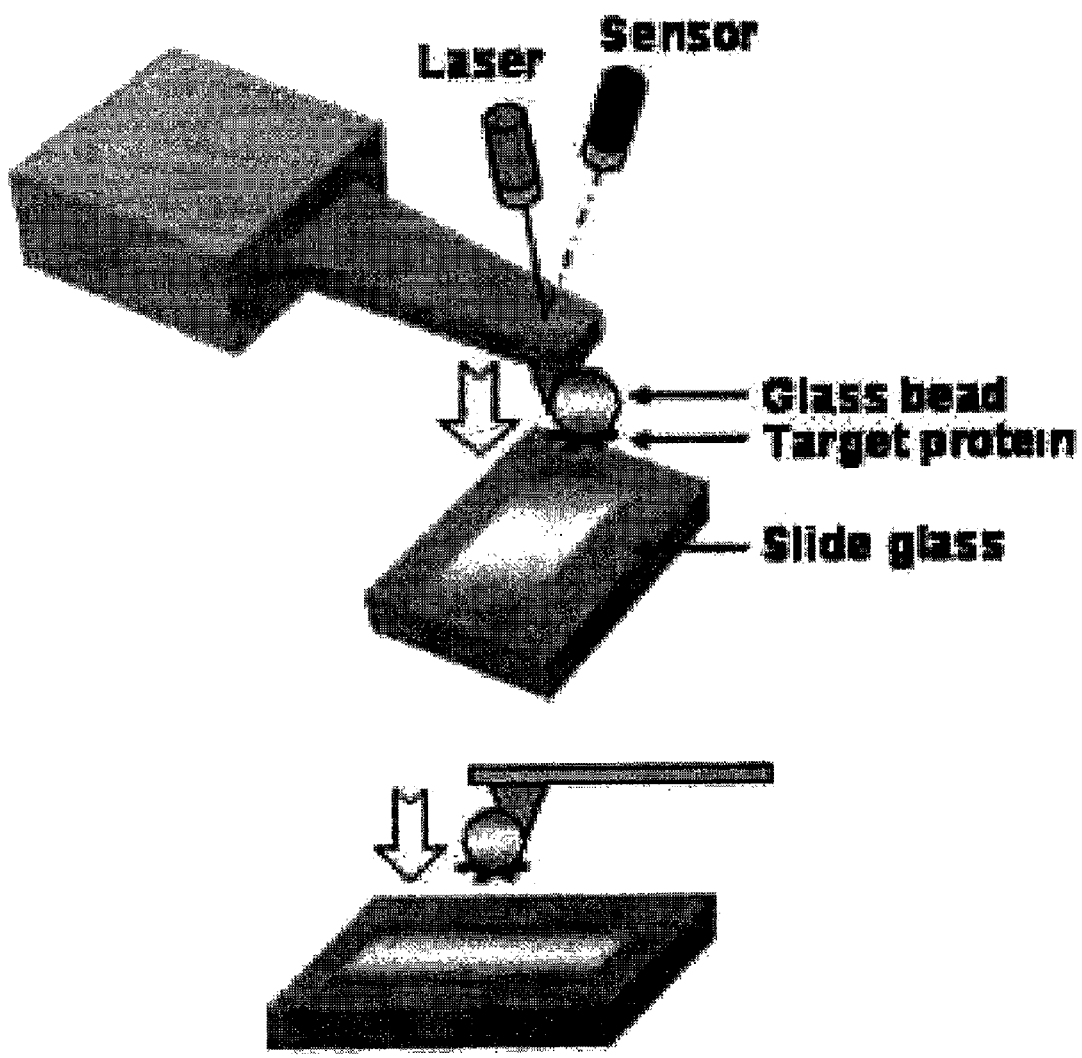
FIG. 17 is a schematic view of a method of using modified atomic force microscopy (AFM) for testing the adherence of recombinant adhesive proteins.

The AFM cantilevers which glass bead was attached to were mounted on the AFM (FIG. 17). To attach the proteins to the glass bead on AFM tip, the glass bead was immersed in 1 µl of tyrosinase-treated protein solutions for 5 minutes and then dried for 10 minutes. The force-distance curve was obtained by contacting the proteins on the AFM cantilever with a clean glass surface.

Figure 18:
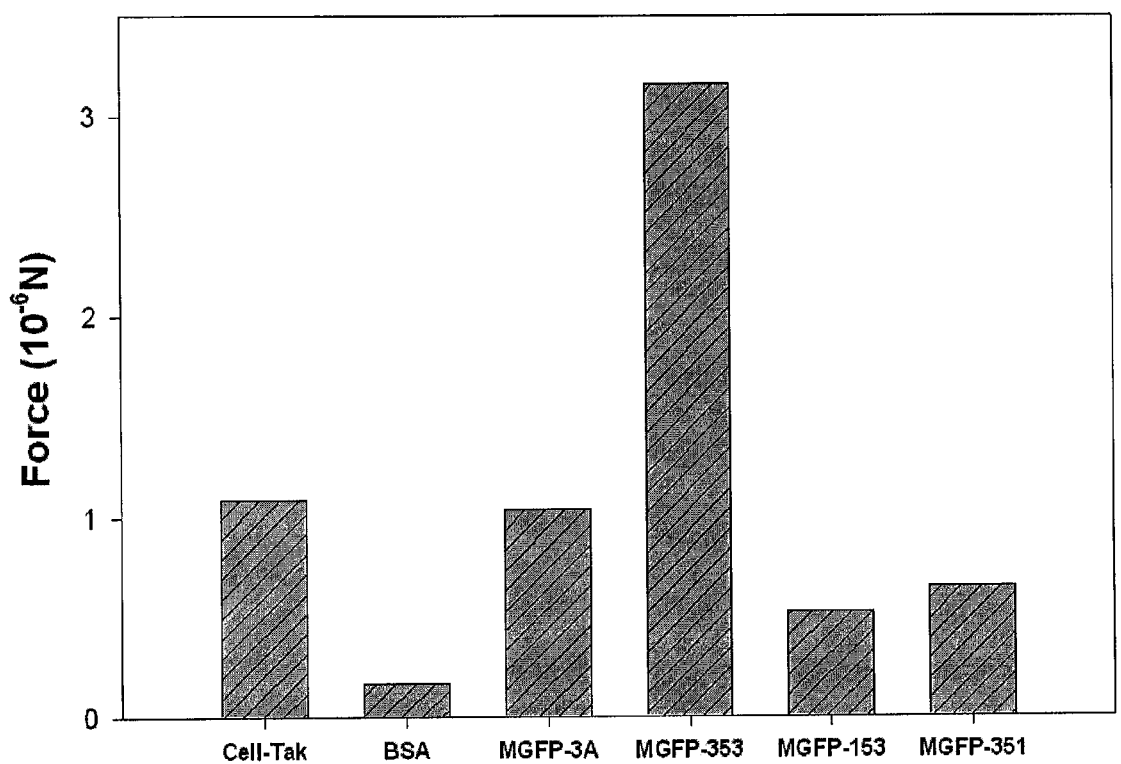
FIG. 18 shows adhesive forces measured with modified AFM for a recombinant protein MGFP-3A MUTANT, MGFP-353, MGFP-153, and MGFP-351 which are modified with tyrosinase.

As a result, the recombinant mussel adhesion protein MGFP-353 had a mean adhesion force of 3.16 µN, which is three times as high as 1.2 µN of Cell-Tak. MGFP-153 and MGFP-351 had lower adhesion force than Cell-Tak and MGFP-3A MUTANT, but can be increased by improving the modification efficiency (FIG. 18). This result suggests that the recombinant mussel adhesion proteins have an adhesion force which is industrially applicable.

Example 12

Measurement of Cell Adhesion Property of the Mussel Adhesive Protein with *Drosophila* S2 Cells

*Drosophila* S2 cells (Invitrogen) used in the test was a cell transfected with pMT/BiP/hEPO [H. S. Shin, H. J. Cha, Biotechnol. Prog., 2002, 16, 1187-1194]. *Drosophila* S2 cells were grown at 27° C. in M3 medium (Shields and Sang M3 insect medium; Sigma, St. Louis, Mo.) containing 10% IMS (insect medium supplement), 1% antibiotic-antimycotic (Invitrogen), and hygromycin 3 µ/mL. Tyrosinase-treated recombinant MGFP-353 protein, recombinant MGFP-351 protein and recombinant MGFP-153 protein prepared from Example 6 were dropped onto sterilized slide glass (20 mm×20 mm, Marienfeld, Germany) and incubated at normal temperature for 1 hour in a laminar flow hood, and then washed twice with PBS. After washing two times with PBS, the coated slide glasses of Cell-Tak, BSA, and MGFP-151 were immersed in 100-mm cell culture dishes containing 10 mL of S2 cells at a concentration of 4×10$^6$ cells/mL for comparing adhesion property.

Figure 19:
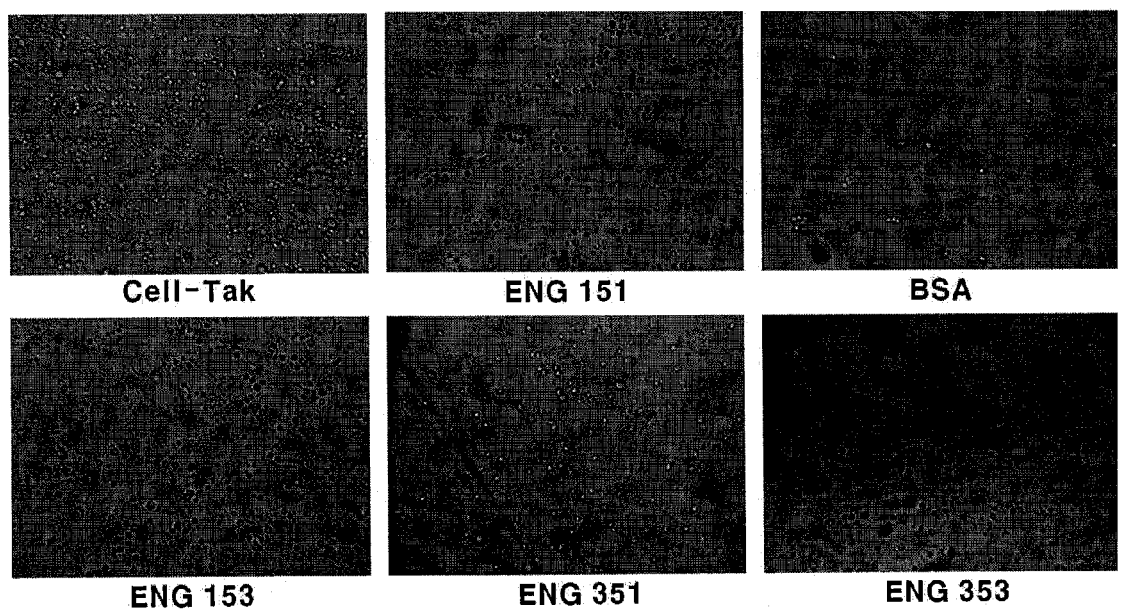
FIG. 19 is a photograph showing adhesion force of recombinant mussel adhesives of GFP-151, MGFP-353, MGFP-153, and MGFP351 to S2 cell, which are compared with BSA and Cell-Tak. The small and round things shown are cells fixed by adhesive proteins.

After incubation of cell culture dishes containing the coated slide glasses at 27° C. for 24 hours, the culture medium were thrown away and washed two times with PBS. Unattached cells were rinsed away with PBS, and cell viability and location of adhered protein was checked by Trypan blue staining. After washing, S2 cells attached onto the protein were observed under a microscope (FIG. 19). As a result, S2 cells were found to attach to regions where recombinant MGFP-353, recombinant MGFP-153 and MGFP-131 proteins were effectively adhesive, and the attached S2 cells continued to survive in their original shape.

This result suggests that recombinant mussel adhesion proteins have an adhesion force which is industrially applicable.

What is claimed is:

1. An isolated adhesive protein comprising:
a peptide selected from the group consisting of an amino acid sequence as shown in SEQ ID NO:20; an amino acid sequence as shown in SEQ ID NO:22; and an amino acid sequence as shown in SEQ ID NO:24.

2. The adhesive protein according to claim 1, wherein the peptide further comprises 6 histidine residues or GST.

3. An adhesive composition the adhesive composition protein according to claim 1 as an active component.

4. The adhesive composition of claim 3, wherein 5% to 100% of the total number of tyrosine residues in the adhesive protein are modified to 3,4-Dihydroxyphenyl-L-alanine (DOPA).

5. The adhesive of claim 3, wherein the adhesive composition adheres to a substrate selected from the group consisting of plastic, glass, metal, eukaryotic cells, prokaryotic cells, and plant cell walls and lipids.

6. The adhesive of claim 5, wherein the adhesive composition is applied to a biological sample.

7. The adhesive composition of claim 3, further comprising at least one oxidant selected from the group consisting of tyrosinase or $H_2O_2$.

* * * * *

UNITED STATES PATENT AND TRADEMARK OFFICE
CERTIFICATE OF CORRECTION

PATENT NO. : 7,947,806 B2
APPLICATION NO. : 11/911004
DATED : May 24, 2011
INVENTOR(S) : Hyung Joon Cha It is certified that error appears in the above-identified patent and that said Letters Patent is hereby corrected as shown below:

In the Specification:

Column 16, line 53, change "MGFP-131" to --MGFP-351--

Signed and Sealed this
Eleventh Day of June, 2013

Teresa Stanek Rea
*Acting Director of the United States Patent and Trademark Office*

SEQUENCE LISTING

<160> NUMBER OF SEQ ID NOS: 25

<210> SEQ ID NO 1
<211> LENGTH: 30
<212> TYPE: DNA

```
<213> ORGANISM: Artificial Sequence
<220> FEATURE:
<223> OTHER INFORMATION: Primer MGFP-3A Mutant-U

<400> SEQUENCE: 1
ggggctagcg ctgattatta tggtccaaag                              30

<210> SEQ ID NO 2
<211> LENGTH: 27
<212> TYPE: DNA
<213> ORGANISM: Artificial Sequence
<220> FEATURE:
<223> OTHER INFORMATION: Primer MGFP-3A Mutant-D

<400> SEQUENCE: 2
cccggatcct taataatact ttcgtcc                                 27

<210> SEQ ID NO 3
<211> LENGTH: 27
<212> TYPE: DNA
<213> ORGANISM: Artificial Sequence
<220> FEATURE:
<223> OTHER INFORMATION: Primer ENG353F1

<400> SEQUENCE: 3
gggcatatgg ctgattatta tggtcca                                 27

<210> SEQ ID NO 4
<211> LENGTH: 27
<212> TYPE: DNA
<213> ORGANISM: Artificial Sequence
<220> FEATURE:
<223> OTHER INFORMATION: Primer ENG353R1

<400> SEQUENCE: 4
cccgaattca taatactttc gtcccca                                 27

<210> SEQ ID NO 5
<211> LENGTH: 27
<212> TYPE: DNA
<213> ORGANISM: Artificial Sequence
<220> FEATURE:
<223> OTHER INFORMATION: Primer ENG353F2

<400> SEQUENCE: 5
ggggaattca gttctgaaga atacaaa                                 27

<210> SEQ ID NO 6
<211> LENGTH: 27
<212> TYPE: DNA
<213> ORGANISM: Artificial Sequence
<220> FEATURE:
<223> OTHER INFORMATION: Primer ENG353R2

<400> SEQUENCE: 6
cccaagctta ctgctaccac ctccata                                 27

<210> SEQ ID NO 7
<211> LENGTH: 27
<212> TYPE: DNA
<213> ORGANISM: Artificial Sequence
<220> FEATURE:
<223> OTHER INFORMATION: Primer ENG353F3

<400> SEQUENCE: 7
gggaagcttg ctgattatta tggtcca                                 27
```

```
<210> SEQ ID NO 8
<211> LENGTH: 30
<212> TYPE: DNA
<213> ORGANISM: Artificial Sequence
<220> FEATURE:
<223> OTHER INFORMATION: Primer ENG353R3

<400> SEQUENCE: 8
gggctcgaga taatactttc gtccccatcg                                           30

<210> SEQ ID NO 9
<211> LENGTH: 27
<212> TYPE: DNA
<213> ORGANISM: Artificial Sequence
<220> FEATURE:
<223> OTHER INFORMATION: Primer ENG153F

<400> SEQUENCE: 9
catcatggta tgcatatggc taaaccg                                              27

<210> SEQ ID NO 10
<211> LENGTH: 27
<212> TYPE: DNA
<213> ORGANISM: Artificial Sequence
<220> FEATURE:
<223> OTHER INFORMATION: Primer ENG153R

<400> SEQUENCE: 10
ttcttcagaa ctggattctt tgtaagt                                              27

<210> SEQ ID NO 11
<211> LENGTH: 27
<212> TYPE: DNA
<213> ORGANISM: Artificial Sequence
<220> FEATURE:
<223> OTHER INFORMATION: Primer ENG351F

<400> SEQUENCE: 11
catcatggta tgaagcttgc taaaccg                                              27

<210> SEQ ID NO 12
<211> LENGTH: 27
<212> TYPE: DNA
<213> ORGANISM: Artificial Sequence
<220> FEATURE:
<223> OTHER INFORMATION: Primer ENG351R

<400> SEQUENCE: 12
ttcttcagaa ctctcgagtt tgtaagt                                              27

<210> SEQ ID NO 13
<211> LENGTH: 138
<212> TYPE: DNA
<213> ORGANISM: Artificial Sequence
<220> FEATURE:
<223> OTHER INFORMATION: MGFP-3A Mutant cDNA
<220> FEATURE:
<221> NAME/KEY: CDS
<222> LOCATION: (1)..(138)

<400> SEQUENCE: 13 gct gat tat tat ggt cca aag tat ggt cct cca aga cgc tac ggt ggt           48
Ala Asp Tyr Tyr Gly Pro Lys Tyr Gly Pro Pro Arg Arg Tyr Gly Gly
 1               5                  10                  15 ggc aac tac aat aga tat ggc aga cgt tat ggc ggg tat aaa ggc tgg           96
Gly Asn Tyr Asn Arg Tyr Gly Arg Arg Tyr Gly Gly Tyr Lys Gly Trp
             20                  25                  30
```

```
aac aat ggt tgg aaa aga ggt cga tgg gga cga aag tat tat         138
Asn Asn Gly Trp Lys Arg Gly Arg Trp Gly Arg Lys Tyr Tyr
            35                  40                  45
```

<210> SEQ ID NO 14
<211> LENGTH: 46
<212> TYPE: PRT
<213> ORGANISM: Artificial Sequence
<220> FEATURE:
<223> OTHER INFORMATION: MGFP-3A Mutant protein

<400> SEQUENCE: 14

```
Ala Asp Tyr Tyr Gly Pro Lys Tyr Gly Pro Pro Arg Arg Tyr Gly Gly
 1               5                  10                  15

Gly Asn Tyr Asn Arg Tyr Gly Arg Arg Tyr Gly Gly Tyr Lys Gly Trp
                20                  25                  30

Asn Asn Gly Trp Lys Arg Gly Arg Trp Gly Arg Lys Tyr Tyr
            35                  40                  45
```

<210> SEQ ID NO 15
<211> LENGTH: 228
<212> TYPE: DNA
<213> ORGANISM: Mytilus galloprovincialis
<220> FEATURE:
<221> NAME/KEY: CDS
<222> LOCATION: (1)..(228)
<223> OTHER INFORMATION: Mytilus galloprovincialis foot protein-5 cDNA

<400> SEQUENCE: 15

```
agt tct gaa gaa tac aaa ggt ggt tat tac cca ggc aat act tac cac         48
Ser Ser Glu Glu Tyr Lys Gly Gly Tyr Tyr Pro Gly Asn Thr Tyr His
 1               5                  10                  15 tat cat tca ggt ggt agt tat cac gga tcc ggc tat cat gga gga tat         96
Tyr His Ser Gly Gly Ser Tyr His Gly Ser Gly Tyr His Gly Gly Tyr
                20                  25                  30 aag gga aag tat tac gga aag gca aag aaa tac tat tat aaa tat aaa         144
Lys Gly Lys Tyr Tyr Gly Lys Ala Lys Lys Tyr Tyr Tyr Lys Tyr Lys
            35                  40                  45 aac agc gga aaa tac aag tat ctg aag aaa gct aga aaa tac cat aga         192
Asn Ser Gly Lys Tyr Lys Tyr Leu Lys Lys Ala Arg Lys Tyr His Arg
    50                  55                  60 aag ggt tac aag aag tat tat gga ggt ggt agc agt                         228
Lys Gly Tyr Lys Lys Tyr Tyr Gly Gly Gly Ser Ser
65                  70                  75
```

<210> SEQ ID NO 16
<211> LENGTH: 76
<212> TYPE: PRT
<213> ORGANISM: Mytilus galloprovincialis

<400> SEQUENCE: 16

```
Ser Ser Glu Glu Tyr Lys Gly Gly Tyr Tyr Pro Gly Asn Thr Tyr His
 1               5                  10                  15

Tyr His Ser Gly Gly Ser Tyr His Gly Ser Gly Tyr His Gly Gly Tyr
                20                  25                  30

Lys Gly Lys Tyr Tyr Gly Lys Ala Lys Lys Tyr Tyr Tyr Lys Tyr Lys
            35                  40                  45

Asn Ser Gly Lys Tyr Lys Tyr Leu Lys Lys Ala Arg Lys Tyr His Arg
    50                  55                  60

Lys Gly Tyr Lys Lys Tyr Tyr Gly Gly Gly Ser Ser
65                  70                  75
```

```
<210> SEQ ID NO 17
<211> LENGTH: 180
<212> TYPE: DNA
<213> ORGANISM: Artificial Sequence
<220> FEATURE:
<223> OTHER INFORMATION: 6 times repeated sequence derived from mytilus
      edulis foot protein-1
<220> FEATURE:
<221> NAME/KEY: CDS
<222> LOCATION: (1)..(180)

<400> SEQUENCE: 17 gct aaa ccg tct tac ccg ccg acc tac aaa gca aaa ccc tcg tac cca      48
Ala Lys Pro Ser Tyr Pro Pro Thr Tyr Lys Ala Lys Pro Ser Tyr Pro
 1               5                  10                  15 ccg act tat aag gct aaa cct agc tat cca cct acg tac aaa gct aaa      96
Pro Thr Tyr Lys Ala Lys Pro Ser Tyr Pro Pro Thr Tyr Lys Ala Lys
             20                  25                  30 ccg tct tac ccg ccg act tac aaa gca aaa ccg tcc tac cct ccg acc     144
Pro Ser Tyr Pro Pro Thr Tyr Lys Ala Lys Pro Ser Tyr Pro Pro Thr
         35                  40                  45 tat aag gct aaa ccg agt tac ccc ccg act tac aaa                     180
Tyr Lys Ala Lys Pro Ser Tyr Pro Pro Thr Tyr Lys
     50                  55                  60

<210> SEQ ID NO 18
<211> LENGTH: 60
<212> TYPE: PRT
<213> ORGANISM: Artificial Sequence
<220> FEATURE:
<223> OTHER INFORMATION: 6 times repeated sequence derived from mytilus
      edulis foot protein-1

<400> SEQUENCE: 18

Ala Lys Pro Ser Tyr Pro Pro Thr Tyr Lys Ala Lys Pro Ser Tyr Pro
 1               5                  10                  15

Pro Thr Tyr Lys Ala Lys Pro Ser Tyr Pro Pro Thr Tyr Lys Ala Lys
             20                  25                  30

Pro Ser Tyr Pro Pro Thr Tyr Lys Ala Lys Pro Ser Tyr Pro Pro Thr
         35                  40                  45

Tyr Lys Ala Lys Pro Ser Tyr Pro Pro Thr Tyr Lys
     50                  55                  60

<210> SEQ ID NO 19
<211> LENGTH: 525
<212> TYPE: DNA
<213> ORGANISM: Artificial Sequence
<220> FEATURE:
<223> OTHER INFORMATION: Bioadgesive protein(MGFP-353) coding sequence
<220> FEATURE:
<221> NAME/KEY: CDS
<222> LOCATION: (1)..(525)

<400> SEQUENCE: 19 atg gct gat tat tat ggt cca aag tat ggt cct cca aga cgt tac ggt      48
Met Ala Asp Tyr Tyr Gly Pro Lys Tyr Gly Pro Pro Arg Arg Tyr Gly
 1               5                  10                  15 ggt ggc aac tac aat aga tat ggc aga cgt tat ggc ggg tat aaa ggc      96
Gly Gly Asn Tyr Asn Arg Tyr Gly Arg Arg Tyr Gly Gly Tyr Lys Gly
             20                  25                  30 tgg aac aat ggt tgg aaa aga ggt cga tgg gga cga aag tat tat gaa     144
Trp Asn Asn Gly Trp Lys Arg Gly Arg Trp Gly Arg Lys Tyr Tyr Glu
         35                  40                  45 ttc agt tct gaa gaa tac aaa ggt ggt tat tac cca ggc aat tcg aac     192
Phe Ser Ser Glu Glu Tyr Lys Gly Gly Tyr Tyr Pro Gly Asn Ser Asn
     50                  55                  60
```

```
cac tat cat tca ggt ggt agt tat cac gga tcc ggc tac cat gga gga        240
His Tyr His Ser Gly Gly Ser Tyr His Gly Ser Gly Tyr His Gly Gly
 65                  70                  75                  80 tat aag gga aag tat tac gga aag gca aag aaa tac tat tat aaa tat        288
Tyr Lys Gly Lys Tyr Tyr Gly Lys Ala Lys Lys Tyr Tyr Tyr Lys Tyr
                 85                  90                  95 aaa aac agc gga aaa tac aag tat cta aag aaa gct aga aaa tac cat        336
Lys Asn Ser Gly Lys Tyr Lys Tyr Leu Lys Lys Ala Arg Lys Tyr His
            100                 105                 110 aga aag ggt tac aag aag tat tat gga ggt ggt agc agt aag ctt gct        384
Arg Lys Gly Tyr Lys Lys Tyr Tyr Gly Gly Gly Ser Ser Lys Leu Ala
        115                 120                 125 gat tat tat ggt cca aag tat ggt cct cca aga cgt tac ggt ggt ggc        432
Asp Tyr Tyr Gly Pro Lys Tyr Gly Pro Pro Arg Arg Tyr Gly Gly Gly
    130                 135                 140 aac tac aat aga tat ggc aga cgt tat ggc ggg tat aaa ggc tgg aac        480
Asn Tyr Asn Arg Tyr Gly Arg Arg Tyr Gly Gly Tyr Lys Gly Trp Asn
145                 150                 155                 160 aat ggt tgg aaa aga ggt cga tgg gga cga aag tat tat ctc gag            525
Asn Gly Trp Lys Arg Gly Arg Trp Gly Arg Lys Tyr Tyr Leu Glu
                165                 170                 175

<210> SEQ ID NO 20
<211> LENGTH: 175
<212> TYPE: PRT
<213> ORGANISM: Artificial Sequence
<220> FEATURE:
<223> OTHER INFORMATION: Bioadgesive protein(MGFP-353)

<400> SEQUENCE: 20

Met Ala Asp Tyr Tyr Gly Pro Lys Tyr Gly Pro Pro Arg Arg Tyr Gly
 1               5                  10                  15

Gly Gly Asn Tyr Asn Arg Tyr Gly Arg Arg Tyr Gly Gly Tyr Lys Gly
             20                  25                  30

Trp Asn Asn Gly Trp Lys Arg Gly Arg Trp Gly Arg Lys Tyr Tyr Glu
         35                  40                  45

Phe Ser Ser Glu Glu Tyr Lys Gly Gly Tyr Tyr Pro Gly Asn Ser Asn
     50                  55                  60

His Tyr His Ser Gly Gly Ser Tyr His Gly Ser Gly Tyr His Gly Gly
 65                  70                  75                  80

Tyr Lys Gly Lys Tyr Tyr Gly Lys Ala Lys Lys Tyr Tyr Tyr Lys Tyr
                 85                  90                  95

Lys Asn Ser Gly Lys Tyr Lys Tyr Leu Lys Lys Ala Arg Lys Tyr His
            100                 105                 110

Arg Lys Gly Tyr Lys Lys Tyr Tyr Gly Gly Gly Ser Ser Lys Leu Ala
        115                 120                 125

Asp Tyr Tyr Gly Pro Lys Tyr Gly Pro Pro Arg Arg Tyr Gly Gly Gly
    130                 135                 140

Asn Tyr Asn Arg Tyr Gly Arg Arg Tyr Gly Gly Tyr Lys Gly Trp Asn
145                 150                 155                 160

Asn Gly Trp Lys Arg Gly Arg Trp Gly Arg Lys Tyr Tyr Leu Glu
                165                 170                 175

<210> SEQ ID NO 21
<211> LENGTH: 567
<212> TYPE: DNA
<213> ORGANISM: Artificial Sequence
<220> FEATURE:
<223> OTHER INFORMATION: Bioadhesive protein(MGFP-153) coding sequence
<220> FEATURE:
```

<220> FEATURE:
<221> NAME/KEY: CDS
<222> LOCATION: (1)..(567)
<223> OTHER INFORMATION: Bioadhesive protein(MGFP-153)

<400> SEQUENCE: 21

```
atg gct aaa ccg tct tac ccg ccg act tac aaa gca aaa ccc tcg tac      48
Met Ala Lys Pro Ser Tyr Pro Pro Thr Tyr Lys Ala Lys Pro Ser Tyr
1               5                   10                  15 cca ccg act tat aag gct aaa cct agc tat cca cct acg tac aaa gct      96
Pro Pro Thr Tyr Lys Ala Lys Pro Ser Tyr Pro Pro Thr Tyr Lys Ala
            20                  25                  30 aaa ccg tct tac ccg ccg act tac aaa gca aaa ccg tcc tac cct ccg     144
Lys Pro Ser Tyr Pro Pro Thr Tyr Lys Ala Lys Pro Ser Tyr Pro Pro
        35                  40                  45 acc tat aag gct aaa ccg agt tac ccc ccg act tac aaa gaa ttc agt     192
Thr Tyr Lys Ala Lys Pro Ser Tyr Pro Pro Thr Tyr Lys Glu Phe Ser
    50                  55                  60 tct gaa gaa tac aaa ggt ggt tat tac cca ggc aat tcg aac cac tat     240
Ser Glu Glu Tyr Lys Gly Gly Tyr Tyr Pro Gly Asn Ser Asn His Tyr
65                  70                  75                  80 cat tca ggt ggt agt tat cac gga tcc ggc tac cat gga gga tat aag     288
His Ser Gly Gly Ser Tyr His Gly Ser Gly Tyr His Gly Gly Tyr Lys
                85                  90                  95 gga aag tat tac gga aag gca aag aaa tac tat tat aaa tat aaa aac     336
Gly Lys Tyr Tyr Gly Lys Ala Lys Lys Tyr Tyr Tyr Lys Tyr Lys Asn
            100                 105                 110 agc gga aaa tac aag tat cta aag aaa gct aga aaa tac cat aga aag     384
Ser Gly Lys Tyr Lys Tyr Leu Lys Lys Ala Arg Lys Tyr His Arg Lys
        115                 120                 125 ggt tac aag aag tat tat gga ggt ggt agc agt aag ctt gct gat tat     432
Gly Tyr Lys Lys Tyr Tyr Gly Gly Gly Ser Ser Lys Leu Ala Asp Tyr
    130                 135                 140 tat ggt cca aag tat ggt cct cca aga cgt tac ggt ggt ggc aac tac     480
Tyr Gly Pro Lys Tyr Gly Pro Pro Arg Arg Tyr Gly Gly Gly Asn Tyr
145                 150                 155                 160 aat aga tat ggc aga cgt tat ggc ggg tat aaa ggc tgg aac aat ggt     528
Asn Arg Tyr Gly Arg Arg Tyr Gly Gly Tyr Lys Gly Trp Asn Asn Gly
                165                 170                 175 tgg aaa aga ggt cga tgg gga cga aag tat tat ctc gag             567
Trp Lys Arg Gly Arg Trp Gly Arg Lys Tyr Tyr Leu Glu
            180                 185
```

<210> SEQ ID NO 22
<211> LENGTH: 189
<212> TYPE: PRT
<213> ORGANISM: Artificial Sequence
<220> FEATURE:
<223> OTHER INFORMATION: Bioadhesive protein(MGFP-153)

<400> SEQUENCE: 22

```
Met Ala Lys Pro Ser Tyr Pro Pro Thr Tyr Lys Ala Lys Pro Ser Tyr
1               5                   10                  15

Pro Pro Thr Tyr Lys Ala Lys Pro Ser Tyr Pro Pro Thr Tyr Lys Ala
            20                  25                  30

Lys Pro Ser Tyr Pro Pro Thr Tyr Lys Ala Lys Pro Ser Tyr Pro Pro
        35                  40                  45

Thr Tyr Lys Ala Lys Pro Ser Tyr Pro Pro Thr Tyr Lys Glu Phe Ser
    50                  55                  60

Ser Glu Glu Tyr Lys Gly Gly Tyr Tyr Pro Gly Asn Ser Asn His Tyr
65                  70                  75                  80

His Ser Gly Gly Ser Tyr His Gly Ser Gly Tyr His Gly Gly Tyr Lys
```

```
                     85                  90                  95
Gly Lys Tyr Tyr Gly Lys Ala Lys Lys Tyr Tyr Lys Tyr Lys Asn
            100                 105                 110

Ser Gly Lys Tyr Lys Tyr Leu Lys Lys Ala Arg Lys Tyr His Arg Lys
            115                 120                 125

Gly Tyr Lys Lys Tyr Tyr Gly Gly Ser Ser Lys Leu Ala Asp Tyr
            130                 135                 140

Tyr Gly Pro Lys Tyr Gly Pro Pro Arg Arg Tyr Gly Gly Asn Tyr
145                 150                 155                 160

Asn Arg Tyr Gly Arg Arg Tyr Gly Gly Tyr Lys Gly Trp Asn Asn Gly
                165                 170                 175

Trp Lys Arg Gly Arg Trp Gly Arg Lys Tyr Tyr Leu Glu
            180                 185

<210> SEQ ID NO 23
<211> LENGTH: 588
<212> TYPE: DNA
<213> ORGANISM: Artificial Sequence
<220> FEATURE:
<223> OTHER INFORMATION: Bioadhesive protein(MFGP-351) coding sequence
<220> FEATURE:
<221> NAME/KEY: CDS
<222> LOCATION: (1)..(567)
<223> OTHER INFORMATION: Bioadhesive protein(MGFP-351)

<400> SEQUENCE: 23 atg gct gat tat tat ggt cca aag tat ggt cct cca aga cgt tac ggt        48
Met Ala Asp Tyr Tyr Gly Pro Lys Tyr Gly Pro Pro Arg Arg Tyr Gly
 1               5                  10                  15 ggt ggc aac tac aat aga tat ggc aga cgt tat ggg ggt tat aaa ggc        96
Gly Gly Asn Tyr Asn Arg Tyr Gly Arg Arg Tyr Gly Gly Tyr Lys Gly
             20                  25                  30 tgg aac aat ggt tgg aaa aga ggt cga tgg gga cga aag tat tat gaa       144
Trp Asn Asn Gly Trp Lys Arg Gly Arg Trp Gly Arg Lys Tyr Tyr Glu
         35                  40                  45 ttc agt tct gaa gaa tac aaa ggt ggt tat tac cca ggc aat tcg aac       192
Phe Ser Ser Glu Glu Tyr Lys Gly Gly Tyr Tyr Pro Gly Asn Ser Asn
     50                  55                  60 cac tat cat tca ggt ggt agt tat cac gga tcc ggc tac cat gga gga       240
His Tyr His Ser Gly Gly Ser Tyr His Gly Ser Gly Tyr His Gly Gly
 65                  70                  75                  80 tat aag gga aag tat tac gga aag gca aag aaa tac tat tat aaa tat       288
Tyr Lys Gly Lys Tyr Tyr Gly Lys Ala Lys Lys Tyr Tyr Tyr Lys Tyr
                 85                  90                  95 aaa aac agc gga aaa tac aag tat cta aag aaa gct aga aaa tac cat       336
Lys Asn Ser Gly Lys Tyr Lys Tyr Leu Lys Lys Ala Arg Lys Tyr His
            100                 105                 110 aga aag ggt tac aag aag tat tat gga ggt ggt agc agt aag ctt gct       384
Arg Lys Gly Tyr Lys Lys Tyr Tyr Gly Gly Gly Ser Ser Lys Leu Ala
            115                 120                 125 aaa ccg tct tac ccg ccg acc tac aaa gca aaa ccc tcg tac cca ccg       432
Lys Pro Ser Tyr Pro Pro Thr Tyr Lys Ala Lys Pro Ser Tyr Pro Pro
        130                 135                 140 act tat aag gct aaa cct agc tat cca cct acg tac aaa gct aaa ccg       480
Thr Tyr Lys Ala Lys Pro Ser Tyr Pro Pro Thr Tyr Lys Ala Lys Pro
145                 150                 155                 160 tct tac ccg ccg act tac aaa gca aaa ccg tcc tac cct ccg acc tat       528
Ser Tyr Pro Pro Thr Tyr Lys Ala Lys Pro Ser Tyr Pro Pro Thr Tyr
                165                 170                 175 aag gct aaa ccg agt tac ccc ccg act tac aaa ctc gag            cac   570
Lys Ala Lys Pro Ser Tyr Pro Pro Thr Tyr Lys Leu Glu
```

```
                180              185 caccaccacc accactga                                                588

<210> SEQ ID NO 24
<211> LENGTH: 189
<212> TYPE: PRT
<213> ORGANISM: Artificial Sequence
<220> FEATURE:
<223> OTHER INFORMATION: Bioadhesive protein(MFGP-351)

<400> SEQUENCE: 24

Met Ala Asp Tyr Tyr Gly Pro Lys Tyr Gly Pro Pro Arg Arg Tyr Gly
 1               5                  10                  15

Gly Gly Asn Tyr Asn Arg Tyr Gly Arg Tyr Gly Gly Tyr Lys Gly
            20                  25                  30

Trp Asn Asn Gly Trp Lys Arg Gly Arg Trp Gly Arg Lys Tyr Tyr Glu
        35                  40                  45

Phe Ser Ser Glu Glu Tyr Lys Gly Gly Tyr Tyr Pro Gly Asn Ser Asn
    50                  55                  60

His Tyr His Ser Gly Gly Ser Tyr His Gly Ser Gly Tyr His Gly Gly
65                  70                  75                  80

Tyr Lys Gly Lys Tyr Tyr Gly Lys Ala Lys Tyr Tyr Tyr Lys Tyr
                85                  90                  95

Lys Asn Ser Gly Lys Tyr Lys Tyr Leu Lys Lys Ala Arg Lys Tyr His
            100                 105                 110

Arg Lys Gly Tyr Lys Lys Tyr Tyr Gly Gly Ser Ser Lys Leu Ala
            115                 120                 125

Lys Pro Ser Tyr Pro Pro Thr Tyr Lys Ala Lys Pro Ser Tyr Pro Pro
            130                 135                 140

Thr Tyr Lys Ala Lys Pro Ser Tyr Pro Pro Thr Tyr Lys Ala Lys Pro
145                 150                 155                 160

Ser Tyr Pro Pro Thr Tyr Lys Ala Lys Pro Ser Tyr Pro Pro Thr Tyr
                165                 170                 175

Lys Ala Lys Pro Ser Tyr Pro Pro Thr Tyr Lys Leu Glu
            180                 185

<210> SEQ ID NO 25
<211> LENGTH: 10
<212> TYPE: PRT
<213> ORGANISM: Artificial Sequence
<220> FEATURE:
<223> OTHER INFORMATION: fragment sequence derived from mytilus edulis
      foot protein-1

<400> SEQUENCE: 25

Ala Lys Pro Ser Tyr Pro Pro Thr Tyr Lys
 1               5                  10
```